United States Patent [19]

Peet et al.

[11] Patent Number: 5,208,240
[45] Date of Patent: May 4, 1993

[54] 8-SUBSTITUTED PURINES AS SELECTIVE ADENOSINE RECEPTOR AGENTS

[75] Inventors: Norton P. Peet, Cincinnati; Nelsen L. Lentz, West Chester; Mark W. Dudley, Somerville, all of Ohio

[73] Assignee: Merrell Dow Pharmaceuticals Inc., Cincinnati, Ohio

[21] Appl. No.: 667,943

[22] Filed: Mar. 12, 1991

[51] Int. Cl.$^5$ .................. C07D 473/01; A61K 31/52
[52] U.S. Cl. .................................. 514/263; 514/262; 544/266; 544/267
[58] Field of Search .................. 544/271, 267, 266; 514/262, 263

[56] References Cited

U.S. PATENT DOCUMENTS

| | | | |
|---|---|---|---|
| 4,297,494 | 10/1981 | Gorman et al. | 544/267 |
| 4,299,832 | 11/1981 | Brown et al. | 424/253 |
| 4,397,779 | 8/1983 | Gorman et al. | 260/112.5 R |
| 4,452,788 | 6/1984 | Bristol et al. | 424/253 |
| 4,696,932 | 9/1987 | Jacobson et al. | 514/263 |
| 4,968,672 | 11/1990 | Jacobson et al. | 514/46 |
| 5,047,534 | 9/1991 | Peet et al. | 544/267 |

FOREIGN PATENT DOCUMENTS 31772 11/1964 German Democratic Rep. .

OTHER PUBLICATIONS

Jacobson, et al.: J. Med. Chem. 28, 1334 (1985).
Jacobson, et al.: J. Labelled Compounds and Radiopharm. 23, 519 (1986).
Jacobson, et al.: Molecular Pharmacol. 29, 126 (1986).
Jacobson, et al.: Proc. Natl. Acad. Sci. U.S.A. 83, 4089 (1986).
Williams, et al.: Ann. Rev. Pharmacol. Toxicol. 27, 315 (1987).
Peet et al., "A Novel Synthesis of Xanthines: Support for a New Binding Mode for Xanthines with Respect to Adenosine at Adenosine Receptors", J. Med. Chem. 33, 3127–3130, (1990).

Primary Examiner—Nicholas S. Rizzo
Attorney, Agent, or Firm—Louis J. Wille

[57] ABSTRACT

The present invention relates to certain novel 8-substituted purines as selective $A_1$-adenosine receptor antagonists which are useful in the treatment of patients suffering from Alzheimer's disease, congestive heart failure or pulmonary bronchoconstriction.

13 Claims, No Drawings

8-SUBSTITUTED PURINES AS SELECTIVE ADENOSINE RECEPTOR AGENTS

BACKGROUND OF THE INVENTION

Adenosine has been recognized as an important endogenous regulator of many physiological processes. It has variously been labeled a hormone, a neurotransmitter, a chemical mediator and an intracellular messenger. Its physiological effects are modulated by functional adenosine receptors which are widely distributed in mammalian tissues. There are at least two general classes of adenosine receptors which are involved in the regulation of physiological functions by adenosine including $A_1$-adenosine receptors, which are high affinity receptors which upon activation inhibit adenylate cyclase, and $A_2$-adenosine receptors, which are low affinity receptors which upon activation stimulate adenylate cyclase.

Adenosine has been implicated as a mediator of a wide variety of physiological processes including vasodilitation, cardiac depression, inhibition of lipolysis, vasoconstriction in the kidney, inhibition of platelet aggregation, inhibition of insulin release and potentiation of glucagon release in the pancreas, inhibition of lymphocyte functions, potentiation of histamine release from mast cells, and inhibition of neurotransmitter release from nerve endings. The $A_1$-adenosine receptor is involved in the antilipolytic, cardiac depressant and CNS depressant effects of adenosine. The $A_2$-adenosine receptor is involved in the hypotensive, vasodilatory, antithrombotic and endocrine effects of adenosine.

The wide variety of physiologic effects mediated by the adenosine receptors underscores the great potential utility for selective adenosine receptor agonists and antagonists as therapeutic agents in a variety of disease states. Various adenosine receptor agonists and antagonists have been identified and characterized. For example, the 1,3-dialkylxanthines, such as theophylline, have been shown to possess important therapeutic effects which are linked to their adenosine receptor antagonist activity.

Selective adenosine receptor agonists and antagonists will provide a specific physiological effect which would prove beneficial in a wide variety of disease states. For example, a selective $A_1$-adenosine receptor agonist would inhibit adenylate cyclase and provide a beneficial therapeutic effect by controlling tachycardia or by providing an analgesic, anticonvulsant or antidepressant effect. A selective $A_1$-adenosine receptor antagonist would relieve the inhibition of adenylate cyclase and provide a beneficial therapeutic effect as a cardiotonic agent, a bronchodilator or a cognition enhancing agent. A selective $A_2$-adenosine receptor agonist would stimulate adenylate cyclase and provide a beneficial therapeutic effect as a sedative.

It has now been found that the compounds of the present invention provide a selective $A_1$-adenosine receptor antagonistic effect. These compounds are useful in providing a cardiotonic effect in the treatment of patients suffering from congestive heart failure. These compounds are also useful in providing a cognition enhancing effect in patients suffering from Alzheimer's Disease. Furthermore, these compounds are useful in providing a bronchodilating effect in patients suffering from pulmonary bronchoconstriction.

SUMMARY OF THE INVENTION

The present invention relates to novel [[2,3,6,9-tetrahydro-1,3-dialkyl-2,6-dioxo-1H-purin-8-yl]alkyl]-phenylhetero alkanoic acids and esters of formula (I)

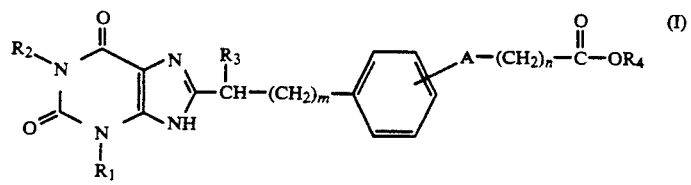

wherein $R_1$, $R_2$ and $R_3$ are each independently a $C_1$-$C_4$ alkyl,
m is an integer 0, 1 or 2,
A is O, S, or NH,
n is an integer 1, 2 or 3, and
$R_4$ is H or a $C_1$-$C_4$ alkyl.

The present invention also relates to novel [[2,3,6,9-tetrahydro-1,3-dialkyl-2,6-dioxo-1H-purin-8-yl]alkyl]-phenylhetero-N-(2-aminoethyl)alkanamides and peptides of formula (II)

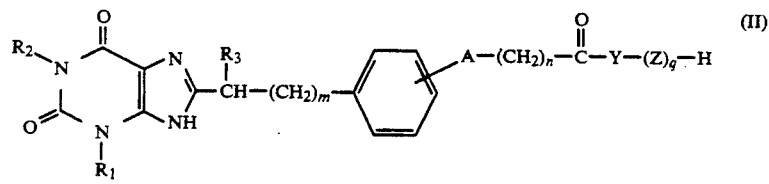

wherein $R_1$, $R_2$ and $R_3$ are each independently a $C_1$-$C_4$ alkyl,
m is an integer 0, 1 or 2,
A is O, S, or NH,
n is an integer 1, 2 or 3,
Y is $-NH(CH_2)_pNH-$,
p is an integer 2, 3 or 4,
Z is a radical of the formula

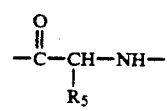

q is an integer 0, 1, 2 or 3, and
$R_5$ is a radical selected each time taken from the group consisting of H, $CH_3$, $-CH(CH_3)_2$, —CH(CH$_3$)CH$_2$CH$_3$,    —CH$_2$CH(CH$_3$)$_2$,
—CH$_2$CH$_2$CH$_2$NH$_2$,    —CH$_2$CH$_2$CH$_2$CH$_2$NH$_2$,
—CH$_2$CH$_2$CH$_2$N=C(NH$_2$)$_2$,
—CH$_2$CH$_2$CH$_2$CH$_2$N=C(NH$_2$)$_2$,

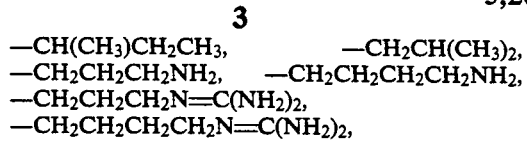

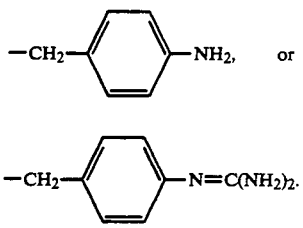

The present invention also relates to novel [[2,3,6,9-tetrahydro-1,3-dialkyl-2,6-dioxo-1H-purin-8-yl]alkyl]-phenylhetero alkanamide peptides of formula (III)

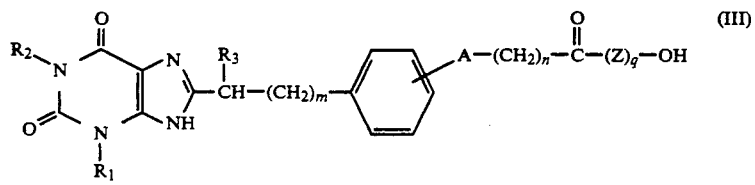

wherein
$R_1$, $R_2$ and $R_3$ are each independently a $C_1$-$C_4$ alkyl,
m is an integer 0, 1 or 2,
A is O, S, or NH,
n is an integer 1, 2 or 3,
Z is a radical of the formula

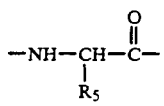

q is an integer 1, 2 or 3, and
$R_5$ is a radical selected each time taken from the group consisting of H, CH$_3$, —CH(CH$_3$)$_2$, —CH(CH$_3$)CH$_2$CH$_3$,    —CH$_2$CH(CH$_3$)$_2$, —CH$_2$CH$_2$CH$_2$NH$_2$,    —CH$_2$CH$_2$CH$_2$CH$_2$NH$_2$,
—CH$_2$CH$_2$CH$_2$N=C(NH$_2$)$_2$,
—CH$_2$CH$_2$CH$_2$CH$_2$N=C(NH$_2$)$_2$,

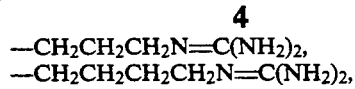

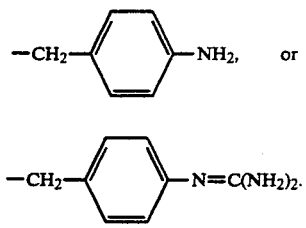

The present invention further relates to a method of providing a selective A$_1$-adenosine receptor antagonist effect in a patient in need thereof comprising administering to said patient a therapeutically effective A$_1$-antagonistic amount of a compound of claim 1, 2 or 3.

DETAILED DESCRIPTION OF THE INVENTION

As used herein the term "$C_1$-$C_4$ alkyl" refers to a saturated straight or branched chain hydrocarbon radical of one to four carbon atoms. Included within the scope of this term are methyl, ethyl, n-propyl, isopropyl, n-butyl, isobutyl and the like. The term "halide", "halo", or "Hal" refers to a chlorine, bromine or iodine atom. The term "hetero" refers to an oxygen, sulfur or nitrogen atom and the term "Pg" refers to a protecting group.

The compounds of formula (I) can be prepared by utilizing procedures and techniques well known and appreciated by one of ordinary skill in the art. A general synthetic scheme for preparing these compounds is set forth in Scheme A wherein all substituents, unless otherwise indicated, are previously defined.

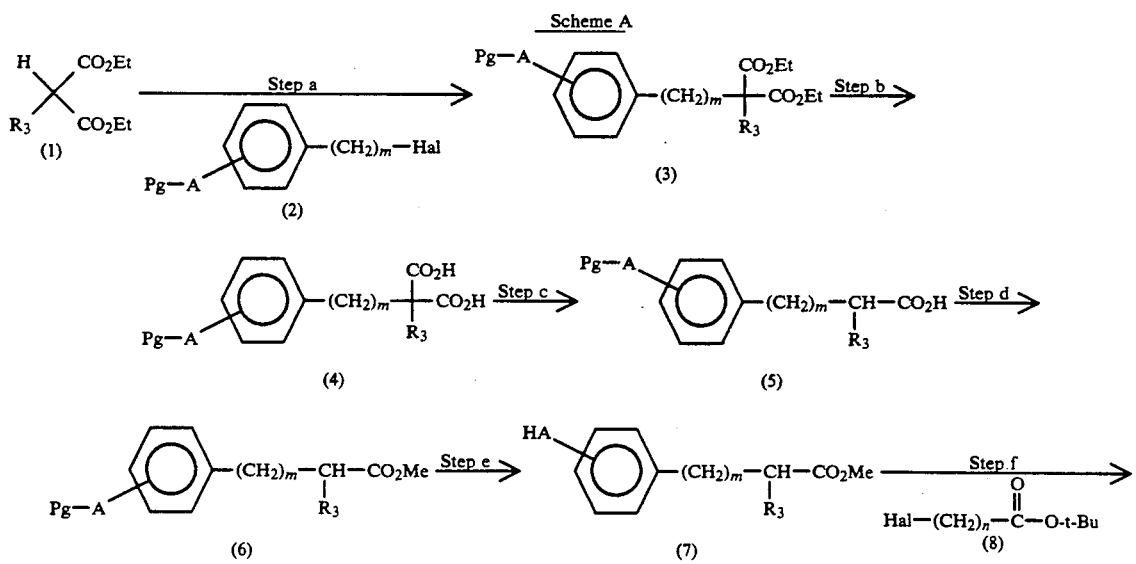

-continued
Scheme A

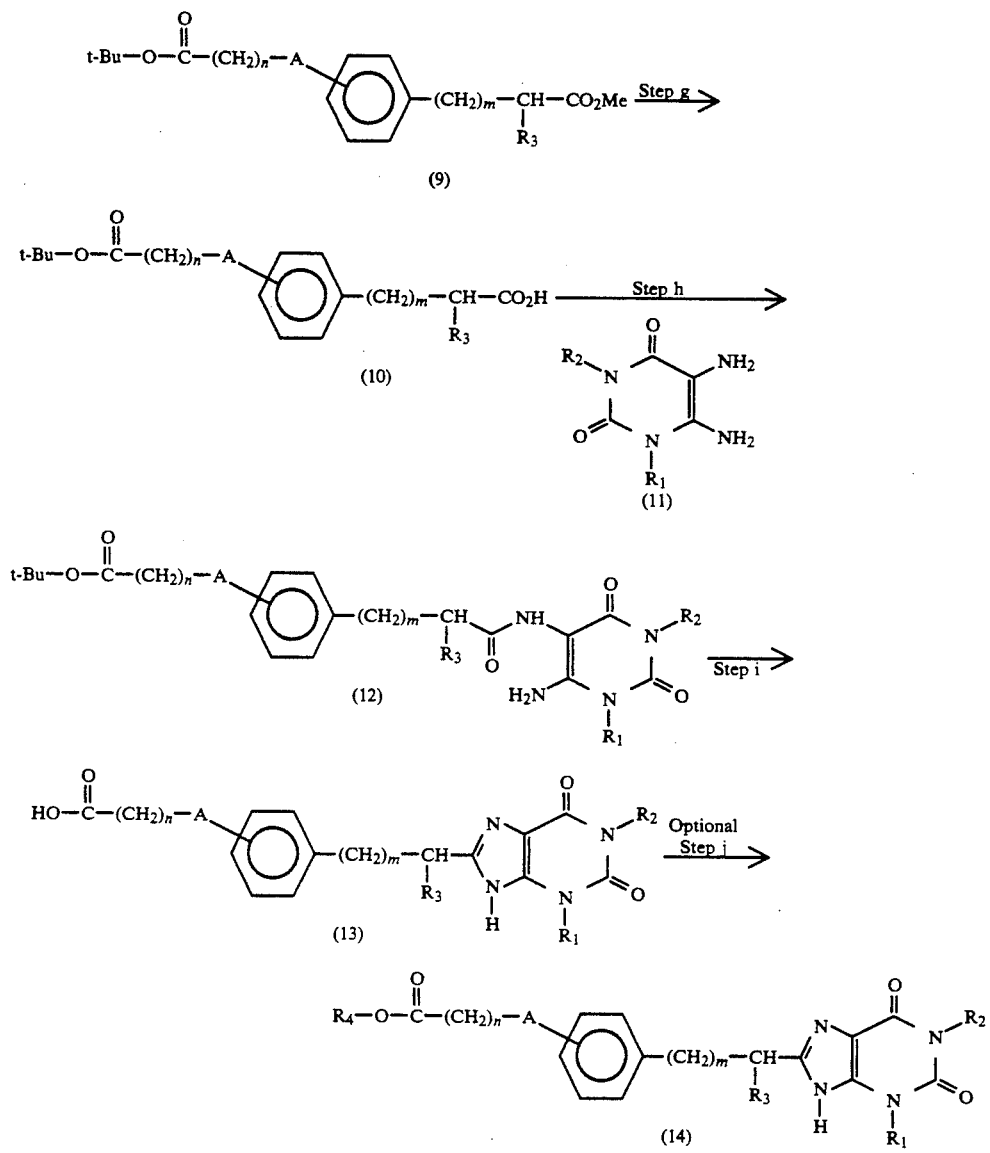

Scheme A provides a general synthetic scheme for preparing compounds of formula (1).

In step a, the appropriate diethyl alkylmalonate of structure (1) is alkylated with the appropriate hetero substituted-(haloalkyl)benzene of structure (2) under basic conditions to give the diethyl dialkyl malonate of structure (3).

For example, the diethyl alkylmalonate of structure (1) is first contacted with a slight molar excess of a suitable non-nucleophilic base, such as sodium hydride, in a suitable aprotic solvent, such as anhydrous tetrahydrofuran. The reaction is typically conducted under an inert atmosphere, such as nitrogen, for a period of time ranging from about 30 minutes to 24 hours and at a temperature range of from about 0° C. to room temperature. A slight molar excess of the appropriate hetero substituted (haloalkyl)benzene of structure (2) is then added. The reaction is typically stirred for a period of time ranging from 30 minutes to 24 hours and at a temperature range of from room temperature to reflux. The diethyl dialkyl malonate of structure (3) can be recovered from the reaction zone by treatment with water and extraction with an organic solvent as is known in the art.

Due to the conditions of the alkylation reaction, it is necessary that the hetero substituted-(haloalkyl)benzene of structure (2) be protected. The selection and utilization of suitable protecting groups are well known to one of ordinary skill in the art and are described in "Protective Groups in Organic Syntheses", Theodora W. Greene, Wiley (1981).

In step b, the appropriate diethyl dialkylmalonate of structure (3) is hydrolyzed under basic conditions to the corresponding dialkyl malonic acid of structure (4). For example, the diethyl dialkylmalonate of structure (3) is contacted with a molar excess of potassium hydroxide. The reactants are typically contacted in a protic solvent system such as ethanol/water. The reactants are typically stirred together for a period of time ranging from about 1 to 6 hours and at a temperature range of room temperature to reflux. The reaction mixture is then acidified with an appropriate acid, such as hydrochloric acid. The dialkylmalonic acid as described by structure (4) can be recovered from the reaction zone by techniques such as filtration.

In step c, the dialkylmalonic acid of structure (4) is decarboxylated to give the corresponding 2-alkyl-alkanoic acid of structure (5). Typically, the dialkylmalonic acid of structure (4) is contacted with a catalytic amount of copper(I) oxide in a suitable organic solvent such as acetonitrile. The reactants are typically stirred together for a period of time ranging from 2 to 24 hours and at a temperature range from room temperature to reflux. The 2-alkyl-alkanoic acid of structure (5) can be recovered from the reaction zone by extractive methods as is known in the art.

In step d, the 2-alkyl-alkanoic acid of structure (5) is esterified under acidic conditions to give the corresponding methyl 2-alkyl-alkanoate of structure (6). For example, the 2-alkyl-alkanoic acid of structure (5) is contacted with a molar excess of methanol and a catalytic amount of sulfuric acid. The reactants are typically stirred together for a period of time ranging from 5-24 hours and at a temperature range of from room temperature to reflux. The methyl 2-alkyl-alkanoate of structure (6) can be recovered from the reaction zone by extractive methods as is known in the art.

In step e, the hetero protecting group functionality of the methyl 2-alkyl-alkanoate of structure (6) is removed to give the unprotected methyl-2-alkyl-alkanoate of structure (7). The removal of protecting groups is well known to one of ordinary skill in the art and is described in "Protective Groups in Organic Syntheses", Theodora W. Greene, Wiley (1981).

In step f, the hetero functionality of the unprotected methyl-2-alkyl-alkanoate of structure (7) is alkylated with the appropriate t-butyl haloalkanoate of structure (8) under basic conditions to give the 1,1-dimethylethoxy-oxoalkylhetero-alpha-alkyl-benzenealkanoic acid, methyl ester of structure (9). For example, the unprotected methyl-2-alkyl-alkanoate of structure (7) is contacted with a molar excess of the appropriate t-butyl haloalkanoate of structure (8), a molar excess of a suitable base, such as potassium carbonate, and a catalytic amount of potassium iodide. The reactants are typically contacted in a organic solvent such as acetone. The reactants are typically stirred together for a period of time ranging from 24 to 200 hours and at a temperature range of from room temperature to reflux. The 1,1-dimethylethoxy-oxoalkylhetero-alpha-alkyl-benzenealkanoic acid, methyl ester of structure (9) is recovered from the reaction zone by extractive methods and purified by silica gel chromatography as is known in the art.

In step g, the methyl ester functionality of the appropriate 1,1-dimethylethoxy-oxoalkylhetero-alpha-alkyl-benzenealkanoic acid, methyl ester of structure (9) can be hydrolyzed to give the corresponding 1,1-dimethylethoxy-oxoalkylhetero-alpha-alkyl-benzenealkanoic acid of structure (10).

One method for carrying out the hydrolysis reaction of step g is to contact the 1,1-dimethylethoxy-oxoalkylhetero-alpha-alkyl-benzenealkanoic acid, methyl ester of structure (9) with an equimolar amount of sodium cyanide. The reactants are typically contacted in a organic solvent such as anhydrous hexamethylphosphoramide. The reactants are typically stirred together for a period of time ranging from 24 to 64 hours and at a temperature range of from room temperature to 70° C. The 1,1-dimethylethoxy-oxoalkylhetero-alpha-alkyl-benzenealkanoic acid of structure (10) is recovered from the reaction zone by extractive methods and purified by silica gel chromatography as is known in the art.

Another method for carrying out the hydrolysis reaction of step g is to contact the 1,1-dimethylethoxy-oxoalkylhetero-alpha-alkyl-benzenealkanoic acid, methyl ester of structure (9) with an molar excess of lithium propyl mercaptide. The reactants are typically contacted in a organic solvent such as anhydrous hexamethylphosphoramide. The reactants are typically stirred together for a period of time ranging from 2 to 24 hours and at a temperature range of from room temperature to 70° C. The 1,1-dimethylethoxy-oxoalkylhetero-alpha-alkyl-benzenealkanoic acid of structure (10) is recovered from the reaction zone by extractive methods and purified by silica gel chromatography as is known in the art.

In order to prepare compounds of formula (I) which are enantiomerically pure, it is necessary to carry out a selective hydrolysis reaction in step g. For example, in order to prepare the (+)-enantiomer of the appropriate compound of formula (I), it is necessary to prepare the (+)-enantiomer of the appropriate 1,1-dimethylethoxy-oxoalkylhetero-alpha-alkyl-benzenealkanoic acid of structure (10). Analogously, in order to prepare the (−)-enantiomer of the appropriate compound of formula (I), it is necessary to prepare the (−)-enantiomer of the appropriate 1,1-dimethylethoxy-oxoalkylhetero-alpha-alkyl-benzenealkanoic acid of structure (10).

For example, the 1,1-dimethylethoxy-oxoalkylhetero-alpha-alkyl-benzenealkanoic acid, methyl ester of structure (9) is typically contacted with a catalytic amount of lipase P-30 to give the (+)-1,1-dimethylethoxy-oxoalkylhetero-alpha-alkyl-benzenealkanoic acid of structure (10) and the unreacted (−)-enantiomer of the 1,1-dimethylethoxy-oxoalkylhetero-alpha-alkyl-benzenealkanoic acid, methyl ester of structure (9). The reactants are typically contacted in a pH 7 phosphate buffer. The reactants are typically stirred together for a period of time ranging from 24 to 48 hours at room temperature. The (+)-1,1-dimethylethoxy-oxoalkylhetero-alpha-alkyl-benzenealkanoic acid of structure (10) and the unreacted (−)-1,1-dimethylethoxy-oxoalkylhetero-alpha-alkyl-benzenealkanoic acid, methyl ester of structure (9) are recovered from the reaction zone by extractive methods and separated by silica gel chromatography as is known in the art.

In order to increase the enantiomeric excess (ee) of the (+)-1,1-dimethylethoxy-oxoalkylhetero-alpha-alkyl-benzenealkanoic acid of structure (10), it is reesterified with diazomethane in ethyl ether, and again subjected to the lipase P-30 hydrolysis.

Similarly, in order to increase the enantiomeric excess of the unreacted (−)-1,1-dimethylethoxy-oxoalkylhetero-alpha-alkyl-benzenealkanoic acid, methyl ester of structure (9), it is again subjected to the lipase hydrolysis as described above and the (+)-1,1-dimethylethoxy-oxoalkylhetero-alpha-alkyl-benzenealkanoic acid of structure (10) is removed from the reaction zone by basic extractive methods, such as with sodium hydrogen carbonate. The (−)-1,1-dimethylethoxy-oxoalkylhetero-alpha-alkyl-benzenealkanoic acid, methyl ester of structure (9) is then hydrolyzed with lithium propyl mercaptide as described above to give the (−)-1,1-dimethylethoxy-oxoalkylhetero-alpha-alkyl-benzenealkanoic acid of structure (10).

In step h, the alkanoic acid functionality of the appropriate 1,1-dimethylethoxy-oxoalkylhetero-alpha-alkyl-benzenealkanoic acid of structure (10) is amidated with a 1,3-dialkyl-5,6-diaminouracil of structure (11) to give the [[[[6-amino-1,3-dialkyl-1,2,3,4-tetrahydro-2,4-dioxo-5-pyrimidinyl]amino]oxoalkyl]phenyl]hetero alkanoic acid, t-butyl ester of structure (12). Typically, the 1,1-dimethylethoxy-oxoalkylhetero-alpha-alkyl-benzenealkanoic acid of structure (10) is contacted with equimolar amounts of a non-nucleophilic base, such as N-methylmorpholine and an activating agent, such as isobutyl chloroformate. The reactants are typically contacted in an anhydrous organic solvent such as tetrahydrofuran. The reactants are typically stirred together for a period of time ranging from 1–5 hours and at a temperature range of from −20° C. to room temperature. The appropriate 1,3-dialkyl-5,6-diaminouracil is then added in an organic solvent, such as dimethylformamide. The reactants are typically stirred together for a period of time ranging from 3–24 hours and at a temperature range of from -20° C. to room temperature. The [[[[6-amino-1,3-dialkyl-1,2,3,4-tetrahydro-2,4-dioxo-5-pyrimidinyl]amino]oxoalkyl]phenyl]hetero alkanoic acid, t-butyl ester of structure (12) is recovered from the reaction zone by extractive methods as is known in the art and purified by silica gel chromatography.

In step i, the [[[[6-amino-1,3-dialkyl-1,2,3,4-tetrahydro-2,4-dioxo-5-pyrimidinyl]amino]oxoalkyl]phenyl]hetero alkanoic acid, t-butyl ester of structure (12) is cyclyzed and the t-butyl ester hydrolyzed to give the [[2,3,6,9-tetrahydro-1,3-dialkyl-2,6-dioxo-1H-purin-8-yl]alkyl] phenylhetero alkanoic acid of structure (13).

One method for carrying out the cyclization and hydrolysis reactions of step i is to contact the [[[[6-amino-1,3-dialkyl-1,2,3,4-tetrahydro-2,4-dioxo-5-pyrimidinyl]amino]oxoalkyl]phenyl]hetero alkanoic acid, t-butyl ester of structure (12) with a molar excess of a base, such as potassium hydroxide. The reactants are typically contacted in a protic solvent, such as ethanol. The reactants are typically stirred together for a period of time ranging from 3–24 hours and at a temperature range of from room temperature to reflux. The [[2,3,6,9-tetrahydro-1,3-dialkyl-2,6-dioxo-1H-purin-8-yl]alkyl]phenylhetero alkanoic acid of structure (13) is recovered from the reaction zone by first acidification and extractive methods as is known in the art. It can be purified by silica gel chromatography.

In order to retain the enantiomeric purity of the [[2,3,6,9-tetrahydro-1,3-dialkyl-2,6-dioxo-1H-purin-8-yl]alkyl]phenylhetero alkanoic acid of structure (13), a multi-step method for carrying out the cyclization and hydrolysis reactions must be utilized.

Typically, the [[[[6-amino-1,3-dialkyl-1,2,3,4-tetrahydro-2,4-dioxo-5-pyrimidinyl]amino]oxoalkyl]phenyl]hetero alkanoic acid, t-butyl ester of structure (12) is first contacted with a molar excess of an alkylating agent, such as triethyloxonium tetrafluoroborate. The reactants are typically contacted in an organic solvent, such as benzene, and stirred together for a period of time ranging from 5-24 hours and at a temperature range of from room temperature to reflux. The intermediate ethyl imino ether of the [[[[6-amino-1,3-dialkyl-1,2,3,4-tetrahydro-2,4-dioxo-5-pyrimidinyl]amino]oxoalkyl]phenyl]hetero alkanoic acid, t-butyl ester of structure (12) is recovered from the reaction zone by evaporation of the solvent and purification by silica gel chromatography.

The ethyl imino ether of the [[[[6-amino-1,3-dialkyl-1,2,3,4-tetrahydro-2,4-dioxo-5-pyrimidinyl]amino]oxoalkyl]phenyl]hetero alkanoic acid, t-butyl ester of structure (12) is then cyclized to the ethyl ester of the [[2,3,6,9-tetrahydro-1,3-dialkyl-2,6-dioxo-1H-purin-8-yl]alkyl]phenylhetero alkanoic acid of structure (13) by heating. Typically, the ethyl imino ether of the [[[[6-amino-1,3-dialkyl-1,2,3,4-tetrahydro-2,4-dioxo-5-pyrimidinyl]amino]oxoalkyl]phenyl]hetero alkanoic acid, t-butyl ester of structure (12) is contacted with an organic solvent, such as benzene and stirred at 80° C. for a period of time ranging from 5–48 hours. The ethyl ester of the [[2,3,6,9-tetrahydro-1,3-dialkyl-2,6-dioxo-1H-purin-8-yl]alkyl]phenylhetero alkanoic acid of structure (13) is recovered from the reaction zone by extractive methods as is known in the art and purified by silica gel chromatography.

The ethyl ester of the [[2,3,6,9-tetrahydro-1,3-dialkyl-2,6-dioxo-1H-purin-8-yl]alkyl]phenylhetero alkanoic acid of structure (13) is then hydrolyzed to the [[2,3,6,9-tetrahydro-1,3-dialkyl-2,6-dioxo-1H-purin-8-yl]alkyl]phenylhetero alkanoic acid of structure (13). The ethyl ester of the [[2,3,6,9-tetrahydro-1,3-dialkyl-2,6-dioxo-1H-purin-8-yl]alkyl]phenylhetero alkanoic acid of structure (13) is contacted with an equimolar amount of a base, such as potassium hydroxide in a protic solvent system, such as ethanol/water. Typically the reactants are stirred together for a period of time ranging from 1–24 hours and at a temperature range of from −10° C. to room temperature. The [[2,3,6,9-tetrahydro-1,3-dialkyl-2,6-dioxo-1H-purin-8-yl]alkyl]phenylhetero alkanoic acid of structure (13) is recovered from the reaction zone by first acidification and extractive methods as is known in the art. It can be purified by silica gel chromatography.

In optional step j, the [[2,3,6,9-tetrahydro-1,3-dialkyl-2,6-dioxo-1H-purin-8-yl]alkyl]phenylhetero alkanoic acid of structure (13) may be esterified to give the [[2,3,6,9-tetrahydro-1,3-dialkyl-2,6-dioxo-1H-purin-8-yl]alkyl]phenylhetero alkanoic acid, alkyl ester of structure (14). Typically, the [[2,3,6,9-tetrahydro-1,3-dialkyl-2,6-dioxo-1H-purin-8-yl]alkyl]phenylhetero alkanoic acid of structure (13) is contacted with a molar excess of an appropriate alcohol and a catalytic amount of an acid, such as concentrated sulfuric acid. The reactants are typically stirred together for a period of time ranging from 5-24 hours and at a temperature range of from room temperature to reflux. The [[2,3,6,9-tetrahydro-1,3-dialkyl-2,6-dioxo-1H-purin-8-yl]alkyl]phenylhetero alkanoic acid, alkyl ester of structure (14) is recovered from the reaction zone by evaporation of the solvent and purification by silica gel chromatography.

An alternative synthetic procedure for the preparation of the 1,1-dimethylethoxy-oxoalkylhetero-alpha-alkyl-benzenealkanoic acid, methyl ester of structure (9'), wherein m=0, for use in the preparation of compounds of formula (I) wherein m=0 is set forth in Scheme B. In Scheme B, all substituents, unless otherwise indicated, are as previously defined.

Scheme B

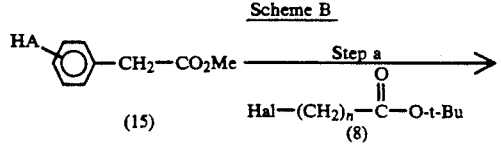

-continued
Scheme B

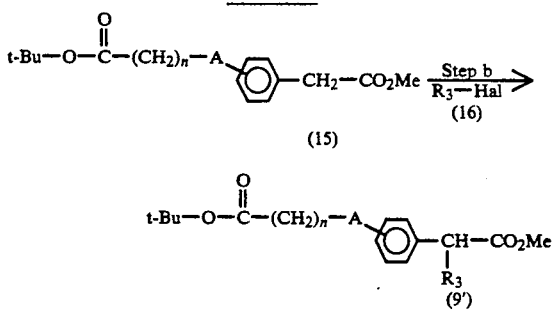

Scheme B provides a general synthetic procedure for the preparation of a 1,1-dimethylethoxy-oxoalkyl-hetero-alpha-alkyl-benzenealkanoic acid, methyl ester of structure (9'), wherein m=0, for use in the preparation of compounds of formula (I) wherein m=0.

In step a, the hetero functionality the methyl phenylacetate of structure (15) is alkylated with the appropriate t-butyl haloalkanoate of structure (8) under basic conditions to give the 1,1-dimethylethoxy-oxoalkyl-hetero-benzenealkanoic acid, methyl ester of structure (15) as described previously in Scheme A, step f.

In step b, the 1,1-dimethylethoxy-oxoalkylhetero-benzenealkanoic acid, methyl ester of structure (15) is alkylated to give the 1,1-dimethylethoxy-oxoalkyl-hetero-alpha-alkyl-benzenealkanoic acid, methyl ester of structure (9'), wherein m=0. The 1,1-dimethylethoxy-oxoalkylhetero-benzenealkanoic acid, methyl ester of structure (15) is typically contacted with a molar excess of a non-nucleophilic base, such as lithium diisopropylamide in a suitable organic solvent, such as hexamethylphosphoramide. The reactants are typically stirred together for a period of time ranging from 15 minutes to 3 hours and at a temperature range of from −78° C. to −20° C. A molar deficiency of an appropriate alkyl halide of structure (16) is then added and the reactants stirred together for a period of time ranging from 3 hours to 24 hours and at a temperature range of from −78° C. to room temperature. The 1,1-dimethylethoxy-oxoalkylhetero-alpha-alkyl-benzenealkanoic acid, methyl ester of structure (9'), wherein m=0 is recovered from the reaction zone by extractive methods as is known in the art. It can be purified by silica gel chromatography.

The compounds of formula (I) wherein m=0 can be prepared from the 1,1-dimethylethoxy-oxoalkylhetero-alpha-alkyl-benzenealkanoic acid, methyl ester of structure (9'), wherein m=0 as described previously in Scheme A, steps g–j.

Starting materials for use in the general synthetic procedures outlined in Schemes A and B are readily available to one of ordinary skill in the art. For example, methyl (p-aminophenyl)acetate is described in *J. Med. Chem.* 26(2) 222-6 1983, certain methyl p-mercaptobenzeneacetates are described in European Patent Application 0106565 (1984) and certain 1,3-dialkyl-5,6-diaminouracils are described in *J. Org. Chemistry.* 16, 1879 1951.

The following examples present typical syntheses as described by Schemes A and B. These examples are understood to be illustrative only and are not intended to limit the scope of the invention in any way. As used in the following examples, the following terms have the meanings indicated: "g" refers to grams, "mmol" refers to millimoles, "mL" refers to milliliters, "°C." refers to degrees Celsius, "TLC" refers to thin layer chromatography, "mg" refers to milligrams, "μL" refers to microliters.

EXAMPLE 1

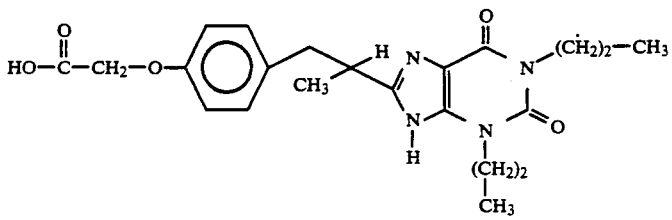

Preparation of
2-[4-[2-(2,3,6,9-Tetrahydro-1,3-dipropyl-2,6-dioxo-1H-purin-8-yl) propyl]phenoxy]acetic acid

Scheme A, Step a: Diethyl methyl-(4-benzyloxy)-benzylmalonate

Suspend sodium hydride (10.1 g, 0.21 mol) in tetrahydrofuran (300 mL), place under a nitrogen atmosphere and cool to 0° C. Add, by dropwise addition, diethyl methylmalonate (34.8 g, 0.2 mol). Stir for 30 minutes at 0° C. and add 4-benzyloxy benzyl chloride (50 g, 0.21 mol). Heat at reflux for 5 hours, cool and pour into water (400 mL). Extract with ethyl acetate (3×600 mL), dry (MgSO$_4$) and evaporate the solvent in vacuo to give the title compound (74.5 g, 100%).

Scheme A, Step b: Methyl-(4-benzyloxy)benzylmalonic acid

Dissolve potassium hydroxide (100 g) in a mixture of water (400 mL) and ethanol (100 mL). Add to diethyl methyl-(4-benzyloxy)benzylmalonate (74.5 g, 0.2 mol) and heat at reflux for 3 hours. Cool to 0° C. and carefully treat with concentrated hydrochloric acid (140 mL) and water (300 mL). Filter the solid and dry to give the title compound (65 g).

Scheme A, Step c: 2-Methyl-3-(4-benzyloxy)phenyl propionic acid

Suspend methyl-(4-benzyloxy)benzylmalonic acid (65 g, 0.2 mol) in acetonitrile (800 mL) and treat with copper(I) oxide (1.5 g, 0.01 mol). Heat at reflux for 7 hours. Cool, filter and evaporate the solvent in vacuo. Take the residue up in ethyl ether (1L) and wash with 10% hydrochloric acid (2×500 mL), water (500 mL) and brine (500 mL). Dry (MgSO$_4$) and evaporate the solvent in vacuo to give the title compound (53.3 g, 98%).

Scheme A, Step d: Methyl [2-methyl-3-(4-benzyloxy)phenyl]propionate

Dissolve 2-methyl-3-(4-benzyloxy)phenyl propionic acid (53.3 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO$_4$) and evaporate the solvent in vacuo to give the title compound (54.2 g, 95%).

Scheme A, Step e: Methyl [2-methyl-3-(4-hydroxy)phenyl]propionate

Dissolve methyl [2-methyl-3-(4-benzyloxy)phenyl]-propionate (13.3 g, 46.8mmol) in methanol (300 mL) and treat with 5% palladium/carbon (1 g). Place under an atmosphere of hydrogen and stir vigorously for 4 hours. Filter through filter aid and evaporate the solvent in vacuo to give the title compound (9.1 g, 100%).

Scheme A, Step f: 4-[[2-(1,1-Dimethylethoxy)-2-oxoethyl]oxy]-alpha-methyl-benzenepropanoic acid, methyl ester Dissolve methyl [2-methyl-3-(4-hydroxy)phenyl]propionate (13.7 g, 70.5 mmol) in acetone (500 mL) and treat with potassium carbonate (10.7 g, 77.6 mmol), potassium iodide (1.17 g, 7.05 mmol) and t-butyl bromoacetate (15.1 g, 77.6 mmol). Reflux for 168 hours, cool, filter and evaporate the solvent in vacuo. Purify by flash chromatography (5→10→15% isopropranol/hexane) to give the title compound (19.84 g).

Scheme A, Step g: 4-[[2-(1,1-Dimethylethoxy)-2-oxoethyl]oxy]-alpha-methyl-benzenepropanoic acid Dissolve 4-[[2-(1,1-dimethylethoxy)-2-oxoethyl]oxy]-alpha-methyl-benzenepropanoic acid, methyl ester (10 g, 32.4 mmol) in anhydrous hexamethylphosphoramide (160 mL) and treat with sodium cyanide (1.59 g, 32.4 mmol). Heat at 70° C. for 48 hours, cool and dilute with saturated ammonium chloride (300 mL). Extract with ethyl ether (400 mL), wash with water (2×300 mL), then brine (300 mL) and dry (MgSO$_4$). Evaporate the solvent in vacuo and purify by flash chromatography (5→10% methanol/chloroform) to give the title compound (1.09 g).

Scheme A, Step h: 2-[[4-[3-[(6-Amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester Dissolve 4-[[2-(1,1-dimethylethoxy)-2-oxoethyl]oxy]-alpha-methyl-benzenepropanoic acid (1.07 g, 3.64 mmol) in tetrahydrofuran (15 mL) and treat with N-methylmorpholine (0.4 mL, 3.64 mmol). Cool to −20° C. and treat with isobutyl chloroformate (0.47 mL, 3.64 mmol). Stir for 30 minutes and add a solution of 1,3-dipropyl-5,6-diaminouracil (0.82 g, 3.64 mmol) in dimethylformamide (5 mL). Stir for 3 hours at −20° C., warm to room temperature and dilute with ethyl ether (200 mL). Separate the organic phase, wash with water (200 mL) and dry (MgSO$_4$). Evaporate the solvent in vacuo and purify by flash chromatography (5→10% methanol/chloroform then 5→10→20% isopropanol/hexane) to yield the title compound (1.66 g).

Scheme A, Step i: 2-[4-[2-(2,3,6,9-Tetrahydro-1,3-dipropyl-2,6-dioxo-1H-purin-8-yl)propyl]phenoxy]acetic acid Dissolve 2-[[4-[3-[(6-amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester (1.6 g, 3.18 mmol) in a mixture of ethanol (30 mL) and 15% potassium hydroxide (30 mL). Heat at 55° C. and stir for 5 hours. Cool, acidify and dilute with water (200 mL). Filter to give 0.69 g crude product. Recrystallize (5% isopropanol/hexane) to give the title compound (0.546 g); mp 168–70° C.

Anal. Calcd for $C_{22}H_{28}N_4O_5$: C, 61.67; H, 6.59; N, 13.08; Found: C, 61.63; H, 6.64; N, 12.77.

EXAMPLE 2

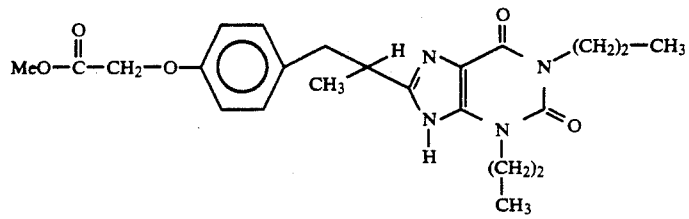

Preparation of 2-[4-[2-(2,3,6,9-Tetrahydro-1,3-dipropyl-2,6-dioxo-1H-purin-8-yl)propyl]phenoxy]acetic acid, methyl ester Dissolve 2-[4-[2-(2,3,6,9-tetrahydro-1,3-dipropyl-2,6-dioxo-1H-purin-8-yl)propyl]phenoxy]acetic acid (85.6 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO$_4$) and evaporate the solvent in vacuo to give the title compound.

EXAMPLE 3

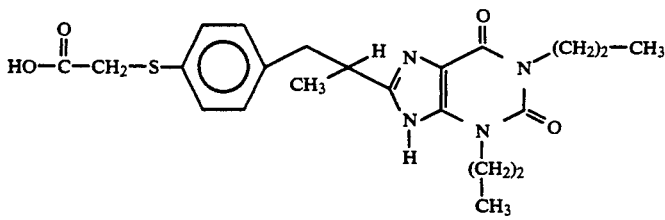

Preparation of
2-[4-[2-(2,3,6,9-Tetrahydro-1,3-dipropyl-2,6-dioxo-1H-purin-8-yl)propyl]phenylthio]acetic acid

Scheme A, Step a: Diethyl methyl-(4-methylthio)benzylmalonate

Suspend sodium hydride (10.1 g, 0.21 mol) in tetrahydrofuran (300 mL), place under a nitrogen atmosphere and cool to 0° C. Add, by dropwise addition, diethyl methylmalonate (34.8 g, 0.2 mol) Stir for 30 minutes at 0° C. and add 4-methylthiobenzyl chloride (36.3 g, 0.21 mol). Heat at reflux for 5 hours, cool and pour into water (400 mL). Extract with ethyl acetate (3×600 mL), dry (MgSO$_4$) and evaporate the solvent in vacuo to give the title compound.

Scheme A, Step b: Methyl-(4-methylthio)benzylmalonic acid

Dissolve potassium hydroxide (100 g) in a mixture of water (400 mL) and ethanol (100 mL). Add to diethyl methyl-(4-methylthio)benzylmalonate (620mg, 0.2 mol) and heat at reflux for 3 hours. Cool to 0° C. and carefully treat with concentrated hydrochloric acid (140 mL) and water (300 mL). Filter the solid and dry to give the title compound.

Scheme A, Step c: 2-Methyl-3-(4-methylthio)phenyl propionic acid

Suspend methyl-(4-methylthio)benzylmalonic acid (508mg, 0.2 mol) in acetonitrile (800 mL) and treat with copper(I) oxide (1.5 g, 0.01 mol). Heat at reflux for 7 hours. Cool, filter and evaporate the solvent in vacuo. Take the residue up in ethyl ether (1L) and wash with 10% hydrochloric acid (2×500 mL), water (500 mL) and brine (500 mL). Dry (MgSO$_4$) and evaporate the solvent in vacuo to give the title compound.

Scheme A, Step d: Methyl [2-methyl-3-(4-methylthio)phenyl]propionate

Dissolve 2-methyl-3-(4-methylthio)phenyl propionic acid (420mg, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO$_4$) and evaporate the solvent in vacuo to give the title compound.

Scheme A, Step e: Methyl [2-methyl-3-(4-thio)phenyl]propionate

Dissolve methyl [2-methyl-3-(4-methylthio)phenyl]-propionate (1.12 g, 5 mmol) in chloroform (20 mL) and treat with metachloroperbenzoic acid (863mg, 5 mmol). Add calcium hydroxide (556mg, 7.5 mmol) and stir for 15 minutes. Filter and evaporate the solvent in vacuo. Dissolve the residue in trifluoroacetic anhydride (10 mL) and heat at reflux for 30 minutes. Evaporate the volatiles in vacuo and dissolve the residue in a mixture of methanol-triethylamine (1:1, 100 mL) and evaporate the solvent in vacuo. Dissolve the residue in chloroform, wash with saturated ammonium chloride and dry (MgSO$_4$). Evaporate the solvent in vacuo to give the title compound.

Scheme A, Step f: 4-[[2-(1,1-Dimethylethoxy)-2-oxoethyl]thio]-alpha-methyl-benzenepropanoic acid, methyl ester Dissolve methyl [2-methyl-3-(4-thio)phenyl]propionate (14.8 g, 70.5 mmol) in acetone (500 mL) and treat with potassium carbonate (10.7 g, 77.6 mmol), potassium iodide (1.17 g, 7.05 mmol) and t-butyl bromoacetate (15.1 g, 77.6 mmol). Reflux for several hours, cool, filter and evaporate the solvent in vacuo. Purify by flash chromatography to give the title compound.

Scheme A, Step g: 4-[[2-(1,1-Dimethylethoxy)-2-oxoethyl]thio]-alpha-methyl-benzenepropanoic acid Dissolve 4-[[2-(1,1-dimethylethoxy)-2-oxoethyl]thio]-alpha-methyl-benzenepropanoic acid, methyl ester (10.5 g, 32.4 mmol) in anhydrous hexamethylphos-phoramide (160 mL) and treat with sodium cyanide (1.59 g, 32.4 mmol). Heat at 70° C. for 48 hours, cool and dilute with saturated ammonium chloride (300 mL). Extract with ethyl ether (400 mL), wash with water (2×300 mL), then brine (300 mL) and dry (MgSO$_4$). Evaporate the solvent in vacuo and purify by flash chromatography to give the title compound.

Scheme A, Step h: 2-[[4-[3-[(6-Amino-1-propyl-1,2,3,4-tetrahydro-3-propyl-2,4-dioxo-5-pyrimidinyl)amino]-2-methyl-3-oxopropyl]phenyl]thio]-acetic acid, 1,1-dimethylethyl ester Dissolve 4-[[2-(1,1-dimethylethoxy)-2-oxoethyl]thio]-alpha-methyl-benzenepropanoic acid (1.13 g, 3.64 mmol) in tetrahydrofuran (15 mL) and treat with N-methylmorpholine (0.4 mL, 3.64 mmol). Cool to −20° C. and treat with isobutyl chloroformate (0.47 mL, 3.64 mmol). Stir for 30 minutes and add a solution of 1,3-dipropyl-5,6-diaminouracil (0.82 g, 3.64 mmol) in dimethylformamide (5 mL). Stir for 3 hours at −20° C., warm to room temperature and dilute with ethyl ether (200 mL). Separate the organic phase, wash with water (200 mL) and dry (MgSO$_4$). Evaporate the solvent in vacuo and purify by flash chromatography to yield the title compound.

Scheme A, Step i: 2-[4-[2-(2,3,6,9-Tetrahydro1,3-dipropyl-2,6-dioxo-1H-purin-8-yl)propyl]phenylthio]acetic acid Dissolve 2-[[4-[3-[(6-amino-1-propyl-1,2,3,4-tetrahydro-3-propyl-2,4-dioxo-5-pyrimidinyl)amino]-2-methyl-3-oxopropyl]phenyl]thio]-acetic acid, 1,1-dimethylethyl ester (1.65 g, 3.18 mmol) in a mixture of ethanol (30 mL)

EXAMPLE 4

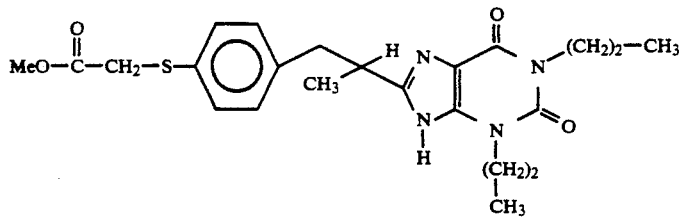

Preparation of
2-[4-[2-(2,3,6,9-Tetrahydro-1,3-dipropyl-2,6-dioxo-1H-purin-8-yl)propyl]phenylthio]acetic acid, methyl ester Dissolve 2-[4-[2-(2,3,6,9-tetrahydro-1,3-dipropyl-2,6-dioxo-1H-purin-8-yl)propyl]phenylthio]acetic acid (88.8 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO₄) and evaporate the solvent in vacuo to give the title compound.

EXAMPLE 5

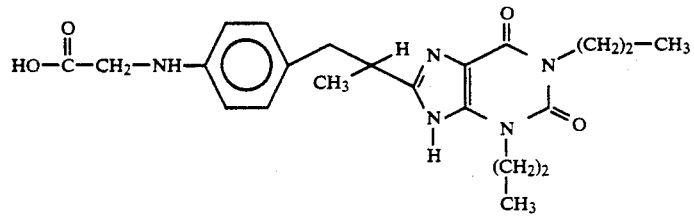

Preparation of
2-[4-[2-(2,3,6,9-Tetrahydro-1,3-dipropyl-2,6-dioxo-1H-purin-8-yl)propyl]phenylamino]acetic acid, Scheme A, Step a: Diethyl methyl-(4-benzylamino)benzylmalonate Suspend sodium hydride (10.1 g, 0.21 mol) in tetrahydrofuran (300 mL), place under a nitrogen atmosphere and cool to 0° C. Add, by dropwise addition, diethyl methylmalonate (34.8 g, 0.2 mol). Stir for 30 minutes at 0° C. and add 4-acetamidobenzyl chloride (38.6 g, 0.21 mol). Heat at reflux for 5 hours, cool and pour into water (400 mL). Extract with ethyl acetate (3×600 mL), dry (MgSO₄) and evaporate the solvent in vacuo to give diethyl methyl-(4-acetamido)benzylmalonate.

Mix diethyl methyl-(4-acetamido)benzylmalonate (5.01 g, 15.6 mmol) and 2N hydrochloric acid (65 mL) and heat at reflux for several hours. Cool to room temperature, basify with solid hydrogen carbonate and extract into ethyl ether (3×). Dry (MgSO₄) and evaporate the solvent in vacuo to give diethyl methyl-(4-amino)benzylmalonate.

Mix diethyl methyl-(4-amino)benzylmalonate (2.01 g, 7.20 mmol) and benzaldehyde (763mg, 7.2 mmol) in acetonitrile (30 mL). Add sodium cyanoborohydride (1.37 g, 23.2 mmol). Add acetic acid as needed to maintain a slightly acidic medium. Stir for several hours, dilute with ethyl ether (100 mL) and wash with 1N sodium hydroxide. Separate the organic phase, dry (MgSO₄) and evaporate the solvent in vacuo. Purify by flash chromatography to give the title compound.

Scheme A, Step b: Methyl-(4-benzylamino)benzylmalonic acid

Dissolve potassium hydroxide (100 g) in a mixture of water (400 mL) and ethanol (100 mL). Add to diethyl methyl-(4-benzylamino)benzylmalonate (73.8 g, 0.2 mol) and heat at reflux for 3 hours. Cool to 0° C. and carefully treat with concentrated hydrochloric acid (140 mL) and water (300 mL). Filter the solid and dry to give the title compound.

Scheme A, Step c: 2-Methyl-3-(4-benzylamino)phenyl propionic acid

Suspend methyl (4-benzylamino)benzylmalonic acid (62.6 g, 0.2 mol) in acetonitrile (800 mL) and treat with copper(I) oxide (1.5 g, 0.01 mol). Heat at reflux for 7 hours. Cool, filter and evaporate the solvent in vacuo. Take the residue up in ethyl ether (1L) and wash with 10% hydrochloric acid (2×500 mL), water (500 mL) and brine (500 mL). Dry (MgSO₄) and evaporate the solvent in vacuo to give the title compound.

Scheme A, Step d: Methyl [2-methyl-3-(4-benzylamino)phenyl]propionate

Dissolve 2-methyl-3-(4-benzylamino)phenyl propionic acid (53.6 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO₄) and evaporate the solvent in vacuo to give the title compound.

Scheme A, Step e: Methyl [2-methyl-3-(4-amino)phenyl]propionate

Dissolve methyl [2-methyl-3-(4-benzylamino)phenyl]propionate (200mg, 0.71 mmol) in formic acid (10 mL of a 4.4% solution in methanol) and add to a suspension to freshly prepared palladium black catalyst (200mg) in formic acid (10 mL of a 4.4% solution in methanol). Stir for several hours under a nitrogen atmosphere, filter and wash with methanol (10 mL) followed by water (10 mL). Combine the filtrate plus the methanol and water washes. Evaporate the solvent in vacuo to give the title compound.

Scheme A, Step f:
4-[[2-(1,1-Dimethylethoxy)-2-oxoethyl]amino]-alpha-methyl-benzenepropanoic acid, methyl ester Dissolve methyl [2-methyl-3-(4-amino)phenyl]propionate (13.6 g, 70.5 mmol) in acetone (500 mL) and treat with potassium carbonate (10.7 g, 77.6 mmol), potassium iodide (1.17 g, 7.05 mmol) and t-butyl bromoacetate (15.1 g, 77.6 mmol). Reflux for several hours, cool, filter and evaporate the solvent in vacuo. Purify by flash chromatography to give the title compound.

Scheme A, Step g:

4-[[2-(1,1-Dimethylethoxy)-2-oxoethyl]amino]-alpha-methyl-benzenepropanoic acid

Dissolve 4-[[2-(1,1-dimethylethoxy)-2-oxoethyl]amino]-alpha-methyl-benzenepropanoic acid, methyl ester (9.95 g, 32.4 mmol) in anhydrous hexamethylphosphoramide (160 mL) and treat with sodium cyanide (1.59 g, 32.4 mmol). Heat at 70° C. for 48 hours, cool and dilute with saturated ammonium chloride (300 mL). Extract with ethyl ether (400 mL), wash with water (2×300 mL), then brine (300 mL) and dry (MgSO₄). Evaporate the solvent in vacuo and purify by flash chromatography to give the title compound.

Scheme A, Step h:
2-[[4-[3-[(6-Amino-1-propyl-1,2,3,4-tetrahydro-3-propyl-2,4-dioxo-5-pyrimidinyl)amino]-2-methyl-3-oxopropyl]phenyl]amino]-acetic acid, 1,1-dimethylethyl ester Dissolve 4-[[2-(1,1-dimethylethoxy)-2-oxoethyl]amino]-alpha-methyl-benzenepropanoic acid (1.07 g, 3.64 mmol) in tetrahydrofuran (15 mL) and treat with N-methylmorpholine (0.4 mL, 3.64 mmol). Cool to −20° C. and treat with isobutyl chloroformate (0.47 mL, 3.64 mmol). Stir for 30 minutes and add a solution of 1,3-dipropyl-5,6-diaminouracil (0.82 g, 3.64 mmol) in dimethylformamide (5 mL). Stir for 3 hours at −20° C., warm to room temperature and dilute with ethyl ether (200 mL). Separate the organic phase, wash with water (200 mL) and dry (MgSO₄). Evaporate the solvent in vacuo and purify by flash chromatography to yield the title compound.

Scheme A, Step i:
2-[4-[2-(2,3,6,9-Tetrahydro-1,3-dipropyl-2,6-dioxo-1H-purin-8-yl)propyl]phenylamino]acetic acid Dissolve 2-[[4-[3-[(6-amino-1-propyl-1,2,3,4-tetrahydro-3-propyl-2,4-dioxo-5-pyrimidinyl)amino]-2-methyl-3-oxopropyl]phenyl]amino]-acetic acid, 1,1-dimethylethyl ester (1.59 g, 3.18 mmol) in a mixture of ethanol (30 mL) and 15% potassium hydroxide (30 mL). Heat at 55° C. and stir for 5 hours. Cool, acidify and dilute with water (200 mL). Filter the precipitate and dry to give the title compound.

EXAMPLE 6

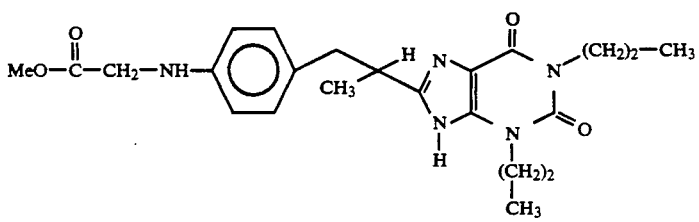

Preparation of
2-[4-[2-(2,3,6,9-Tetrahydro-1,3-dipropyl-2,6-dioxo-1H-purin-8-yl)propyl]phenylamino)acetic acid, methyl ester Dissolve 2-[4-[2-(2,3,6,9-tetrahydro-1,3-dipropyl-2,6-dioxo-1H-purin-8-yl)propyl]phenylamino]acetic acid (85.4 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO₄) and evaporate the solvent in vacuo to give the title compound.

EXAMPLE 7

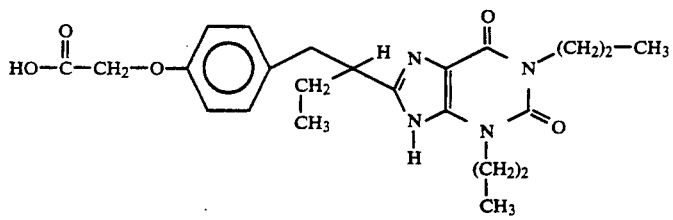

Preparation of
2-[4-[1-(2,3,6,9-Tetrahydro-1,3-dipropyl-2,6-dioxo-1H-purin-8-yl)propyl]phenoxy]acetic acid Scheme B, Step a: Methyl 4-(t-butylacetyloxy)phenylacetate Dissolve methyl 4-hydroxyphenylacetate (15 g, 90.3 mmol) in acetone (300 mL). Add potassium carbonate (13.7 g, 99.3 mmol), potassium iodide (1.47 g, 9.03 mmol) and t-butyl bromoacetate (16 mL, 99.3 mmol). Heat at reflux for 20 hours then remove 200 mL of acetone in vacuo. Dilute the residue with ethyl ether (500 mL), wash with water (2×300 mL) and brine (300 mL). Dry (MgSO₄) and evaporate the solvent in vacuo.

Purify by flash chromatography (30→50% ethyl acetate/hexane) to give the title compound (25.79 g).

Scheme B, Step b:
4-[[2-(1,1-Dimethylethoxy)-2-oxoethyl]oxy-alpha-ethyl-benzeneacetic acid, methyl ester Mix lithium diisopropylamide (51 mmol) and hexamethylphosphoramide (16.5 g, 92 mmol), cool to −78° C. and place under a nitrogen atmosphere. Add a solution of methyl 4-(t-butylacetyloxy)phenylacetate (12.9 g, 46 mmol) in tetrahydrofuran (50 mL) and stir for 30 minutes. Add ethyl bromide (5 g, 46 mmol) and stir at −78° C. for 4 hours. Add saturated ammonium chloride (200 mL) and warm to room temperature. Add water (100 mL), separate the organic phase and extract the aqueous phase with ethyl ether (3×200 mL). Dry (Na$_2$SO$_4$) and evaporate the solvent in vacuo. Purify by flash chromatography (10→20% ethyl acetate/hexane) to give the title compound (5.57 g).

Scheme A, Step g:
4-[[2-(1,1-Dimethylethoxy)-2-oxoethyl]oxy-alpha-ethyl-benzeneacetic acid Suspend lithium hydride (1.01 g, 126.4 mmol) in hexamethylphosphoramide (50 mL) and treat with 1-propanethiol (11.5 mL, 126.4 mmol). Stir for 1.5 hours and add to a solution of 4-[[2-(1,1-dimethylethoxy)-2-oxoethyl]oxy-alpha-ethyl-benzeneacetic acid, methyl ester (5.57 g, 18.06 mmol) in hexamethylphosphoramide (50 mL) under a nitrogen atmosphere. Stir for 20 hours and pour into ice cold 5% hydrochloric acid (500 mL). Extract into ethyl ether (4×300 mL), wash with water (500 mL) and dry (MgSO$_4$). Evaporate the solvent in vacuo and purify by flash chromatography (5→10→20% isopropanol/hexane) to give the title compound (4.01 g).

Scheme A, Step h:
2-[[4-[2-[(6-Amino-1-propyl-1,2,3,4-tetrahydro-3-propyl-2,4-dioxo-5-pyrimidinyl)amino]-1-ethyl-3-oxoethyl]phenyl]oxy]-acetic acid, 1,1-dimethylethyl ester Dissolve 4-[[2-(1,1-dimethylethoxy)-2-oxoethyl]oxy-alpha-ethyl-benzeneacetic acid (4.0 g, 13.59 mmol) in tetrahydrofuran (100 mL) and treat with N-methylmorpholine (1.6 mL, 13.59 mmol). Cool to −20° C. and treat with isobutyl chloroformate (1.8 mL, 13.59 mmol). Stir for 45 minutes and add a solution of 1,3-dipropyl-5,6-diaminouracil (3.1 g, 13.59 mmol) in dimethylformamide (8 mL). Stir for 3 hours at −20° C., warm to room temperature and dilute with chloroform (400 mL). Separate the organic phase, wash with saturated sodium hydrogen carbonate (200 mL), then brine (300 mL). Dry (MgSO$_4$) and evaporate the solvent in vacuo. Purify by flash chromatography (5→10 methanol/chloroform) to give the title compound (5.58 g).

Scheme A, Step i:
2-[4-[1-(2,3,6,9-Tetrahydro-1,3-dipropyl-2,6-dioxo-1H-purin-8-yl)propyl]phenoxy]acetic acid Dissolve 2-[[4-[2-[(6-amino-1-propyl-1,2,3,4-tetrahydro-3-propyl-2,4-dioxo-5-pyrimidinyl)amino]-1-ethyl-3-oxoethyl]phenyl]amino]-acetic acid, 1,1-dimethylethyl ester (5.57 g, 11 mmol) in ethanol (60 mL) and treat with 15% potassium hydroxide (60 mL). Heat at 55° C. for 6 hours, cool to 0° C. and acidify with concentrated hydrochloric acid (15 mL) and water (200 mL). Extract with chloroform (3×200 mL), dry (MgSO$_4$) and evaporate the solvent in vacuo.

Purify by flash chromatography (5→10→20% isopropanol/hexane) to give 2.5 g crude product. Triturate with 10% isopropanol/hexane and dry to give the title compound (369mg); mp 220-25° C. (dec).

EXAMPLE 8

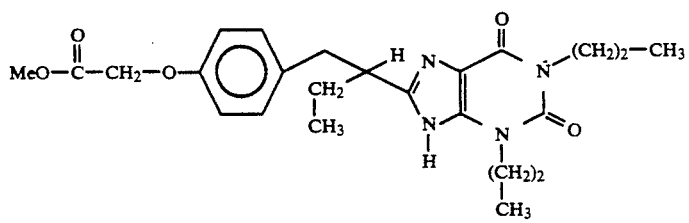

Preparation of 2-[4-[1-(2,3,6,9-Tetrahydro-1,3-dipropyl-2,6-dioxo-1H-purin-8-yl)propyl]phenoxy]acetic acid, methyl ester Dissolve 2-[4-[1-(2,3,6,9-tetrahydro-1,3-dipropyl-2,6-dioxo-1H-purin-8-yl)propyl]phenoxy]acetic acid (85.6 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO$_4$) and evaporate the solvent in vacuo to give the title compound.

EXAMPLE 9

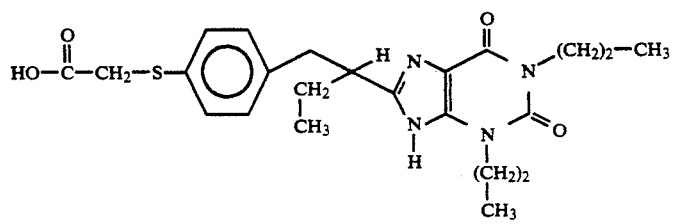

Preparation of
2-[4-[1-(2,3,6,9-Tetrahydro-1,3-dipropyl-2,6-dioxo-1H-purin-8-yl)propyl]phenylthio]acetic acid

Scheme B, Step a: Methyl 4-(t-butylacetylthio)phenylacetate

Dissolve methyl 4-mercaptophenylacetate (16.4 g, 90.3 mmol) in acetone (300 mL). Add potassium carbonate (13.7 g, 99.3 mmol), potassium iodide (1.47 g, 9.03 mmol) and t-butylbromoacetate (16 mL, 99.3 mmol). Heat at reflux for 20 hours then remove 200 mL of acetone in vacuo. Dilute the residue with ethyl ether (500 mL), wash with water (2×300 mL) and brine (300 mL). Dry (MgSO₄) and evaporate the solvent in vacuo. Purify by flash chromatography to give the title compound.

Scheme B, Step b:
4-[[2-(1,1-Dimethylethoxy)-2-oxoethyl]thio-alpha-ethyl-benzeneacetic acid, methyl ester Mix lithium diisopropylamide (51 mmol) and hexamethylphosphoramide (16.5 g, 92 mmol), cool to −78° C. and place under a nitrogen atmosphere. Add a solution of methyl 4-(t-butylacetylthio)phenylacetate (13.6 g, 46 mmol) in tetrahydrofuran (50 mL) and stir for 30 minutes. Add ethyl bromide (5 g, 46 mmol) and stir at −78° C. for 4 hours. Add saturated ammonium chloride (200 mL) and warm to room temperature. Add water (100 mL), separate the organic phase and extract the aqueous phase with ethyl ether (3×200 mL). Dry (Na₂SO₄) and evaporate the solvent in vacuo. Purify by flash chromatography to give the title compound.

Scheme A, Step g:
4-[[2-(1,1-Dimethylethoxy)-2-oxoethyl]thio-alpha-ethyl-benzeneacetic acid Suspend lithium hydride (1.01 g, 126.4 mmol) in hexamethylphosphoramide (50 mL) and treat with 1-propanethiol (11.5 mL, 126.4 mmol). Stir for 1.5 hours and add to a solution of 4-[[2-(1,1-dimethylethoxy)-2-oxoethyl]thio-alpha-ethyl-benzeneacetic acid, methyl ester (5.85 g, 18.06 mmol) in hexamethylphosphoramide (50 mL) under a nitrogen atmosphere. Stir for 20 hours and pour into ice cold 5% hydrochloric acid (500 mL). Extract into ethyl ether (4×300 mL), wash with water (500 mL) and dry (MgSO₄). Evaporate the solvent in vacuo and purify by flash chromatography to give the title compound.

Scheme A, Step h:
2-[[4-[2-[(6-Amino-1-propyl-1,2,3,4-tetrahydro-3-propyl-2,4-dioxo-5-pyrimidinyl)amino]-1-ethyl-3-oxoethyl]phenyl]thio]-acetic acid, 1,1-dimethylethyl ester Dissolve 4-[[2-(1,1-dimethylethoxy)-2-oxoethyl]thio-alpha-ethyl-benzeneacetic acid (4.21 g, 13.59 mmol) in tetrahydrofuran (100 mL) and treat with N-methylmorpholine (1.6 mL, 13.59 mmol). Cool to −20° C. and treat with isobutyl chloroformate (1.8 mL, 13.59 mmol). Stir for 45 minutes and add a solution of 1,3-dipropyl-5,6-diaminouracil (3.1 g, 13.59 mmol) in dimethylformamide (8 mL). Stir for 3 hours at −20° C., warm to room temperature and dilute with chloroform (400 mL). Separate the organic phase, wash with saturated sodium hydrogen carbonate (200 mL), then brine (300 mL). Dry (MgSO₄) and evaporate the solvent in vacuo. Purify by flash chromatography to give the title compound.

Scheme A, Step i:
2-[4-[1-(2,3,6,9-Tetrahydro-1,3-dipropyl-2,6-dioxo-1H-purin-8-yl) propyl]phenylthio]acetic acid Dissolve 2-[[4-[2-[(6-amino-1-propyl-1,2,3,4-tetrahydro-3-propyl-2,4-dioxo-5-pyrimidinyl)amino]-1-ethyl-3-oxoethyl]phenyl]thio]-acetic acid, 1,1-dimethylethyl ester (5.70 g, 11 mmol) in ethanol (60 mL) and treat with 15% potassium hydroxide (60 mL). Heat at 55° C. for 6 hours, cool to 0° C. and acidify with concentrated hydrochloric acid (15 mL) and water (200 mL). Extract with chloroform (3×200 mL), dry (MgSO₄) and evaporate the solvent in vacuo. Purify by flash chromatography to give the title compound.

EXAMPLE 10

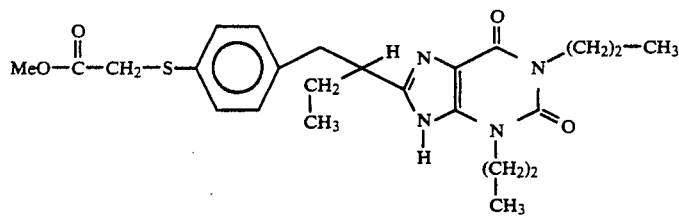

Preparation of
2-[4-[1-(2,3,6,9-Tetrahydro-1,3-dipropyl-2,6-dioxo-1H-purin-8-yl)propyl]phenylthio]acetic acid, methyl ester Dissolve 2-[4-[1-(2,3,6,9-tetrahydro-1,3-dipropyl-2,6-dioxo-1H-purin-8-yl)propyl]phenylthio]acetic acid (88.8 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO₄) and evaporate the solvent in vacuo to give the title compound.

EXAMPLE 11

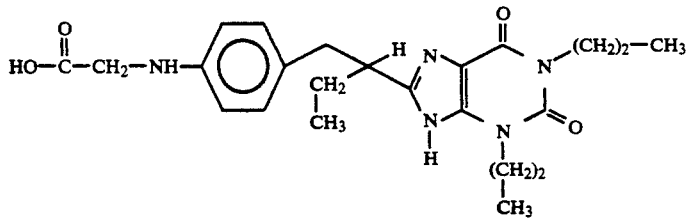

Preparation of
2-[4-[1-(2,3,6,9-Tetrahydro-1,3-dipropyl-2,6-dioxo-1H-purin-8-yl)propyl]phenylamino]acetic acid

Scheme B, Step a: Methyl 4-(t-butylacetylamino)-phenylacetate

Dissolve methyl (4-aminophenyl)acetate (14.9 g, 90.3 mmol) in acetone (300 mL). Add potassium carbonate (13.7 g, 99.3 mmol), potassium iodide (1.47 g, 9.03 mmol) and t-butyl bromoacetate (16 mL, 99.3 mmol). Heat at reflux for 20 hours then remove 200 mL of acetone in vacuo. Dilute the residue with ethyl ether (500 mL), wash with water (2×300 mL) and brine (300 mL). Dry (MgSO₄) and evaporate the solvent in vacuo. Purify by flash chromatography to give the title compound.

Scheme B, Step b:
4-[[2-(1,1-Dimethylethoxy)-2-oxoethyl]amino-alpha-ethyl-benzeneacetic acid, methyl ester Mix lithium diisopropylamide (51 mmol) and hexamethylphosphoramide (16.5 g, 92 mmol), cool to −78° C. and place under a nitrogen atmosphere. Add a solution of methyl 4-(t-butylacetylamino)phenylacetate (6.42 g, 23 mmol) in tetrahydrofuran (50 mL) and stir for 30 minutes. Add ethyl bromide (5 g, 46 mmol) and stir at −78° C. for 4 hours. Add saturated ammonium chloride (200 mL) and warm to room temperature. Add water (100 mL), separate the organic phase and extract the aqueous phase with ethyl ether (3×200 mL). Dry (Na₂SO₄) and evaporate the solvent in vacuo. Purify by flash chromatography to give the title compound.

Scheme A, Step g:
4-[[2-(1,1-Dimethylethoxy)-2-oxoethyl]amino-alpha-ethyl-benzeneacetic acid Suspend lithium hydride (1.01 g, 126.4 mmol) in hexamethylphosphoramide (50 mL) and treat with 1-propanethiol (11.5 mL, 126.4 mmol). Stir for 1.5 hours and add to a solution of 4-[[2-(1,1-dimethylethoxy)-2-oxoethyl]amino-alpha-ethyl-benzeneacetic acid, methyl ester (2.77 g, 9.03 mmol) in hexamethylphosphoramide (50 mL) under a nitrogen atmosphere. Stir for 20 hours and pour into ice cold 5% hydrochloric acid (500 mL). Extract into ethyl ether (4×300 mL), wash with water (500 mL) and dry (MgSO₄). Evaporate the solvent in vacuo and purify by flash chromatography to give the title compound.

Scheme A, Step h:
2-[[4-[2-[(6-Amino-1-propyl-1,2,3,4-tetrahydro-3-propyl-2,4-dioxo-5-pyrimidinyl)amino]-1-ethyl-3-oxoethyl]phenyl]amino]-acetic acid, 1,1-dimethylethyl ester Dissolve 4-[[2-(1,1-dimethylethoxy)-2-oxoethyl]amino-alpha-ethyl-benzeneacetic acid (3.98 g, 13.59 mmol) in tetrahydrofuran (100 mL) and treat with N-methylmorpholine (1.6 mL, 13.59 mmol). Cool to −20° C. and treat with isobutyl chloroformate (1.8 mL, 13.59 mmol). Stir for 45 minutes and add a solution of 1,3-dipropyl-5,6-diaminouracil (3.1 g, 13.59 mmol) in dimethylformamide (8 mL). Stir for 3 hours at −20° C., warm to room temperature and dilute with chloroform (400 mL). Separate the organic phase, wash with saturated sodium hydrogen carbonate (200 mL), then brine (300 mL). Dry (MgSO₄) and evaporate the solvent in vacuo. Purify by ion-exchange chromatography to give the title compound.

Scheme A, Step i:
2-[4-[1-(2,3,6,9-Tetrahydro-1,3-dipropyl-2,6-dioxo-1H-purin-8-yl)propyl]phenylamino]acetic acid Dissolve 2-[[4-[2-[(6-amino-1-propyl-1,2,3,4-tetrahydro-3-propyl-2,4-dioxo-5-pyrimidinyl)amino]-1-ethyl-3-oxoethyl]phenyl]amino]-acetic acid, 1,1-dimethylethyl ester (5.51 g, 11 mmol) in ethanol (60 mL) and treat with 15% potassium hydroxide (60 mL). Heat at 55° C. for 6 hours, cool to 0° C. and acidify with concentrated hydrochloric acid (15 mL) and water (200 mL). Extract with chloroform (3×200 mL), dry (MgSO₄) and evaporate the solvent in vacuo. Purify by flash chromatography to give the title compound.

EXAMPLE 12

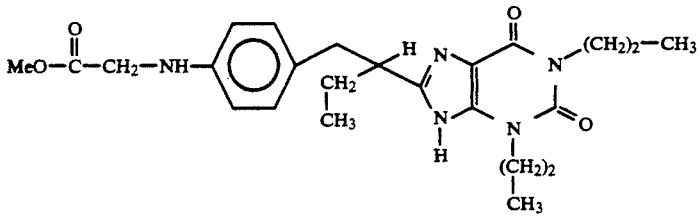

Preparation of
2-[4-[1-(2,3,6,9-Tetrahydro-1,3-dipropyl-2,6-dioxo-1H-purin-8-yl)propyl]phenylamino]acetic acid, methyl ester Dissolve 2-[4-[1-(2,3,6,9-tetrahydro-1,3-dipropyl-2,6-dioxo-1H-purin-8-yl)propyl]phenylamino]acetic acid (85.49, 0.2 mol) in methanol (500 mL) and treat with concentrated sulfuric acid (0.5 mL). Heat to 60° C for 16 hours, cool and reduce the solvent by 50% in vacuo.

Dilute with ethyl ether (500 mL), wash with saturated sodium hydrogen carbonate, then brine. Dry (MgSO4) and evaporate the solvent in vacuo to give the title compound.

EXAMPLE 13

Preparation of
(+)-2-[4-[2-(2,3,6,9-Tetrahydro-1,3-dipropyl-2,6-dioxo-1H-purin-8-yl)propyl]phenylamino]acetic acid Scheme A, step g:
(+)-4-[[2-(1,1-Dimethylethoxy)-2-oxoethyl]oxy]-alpha-methyl-benzenepropanoic acid

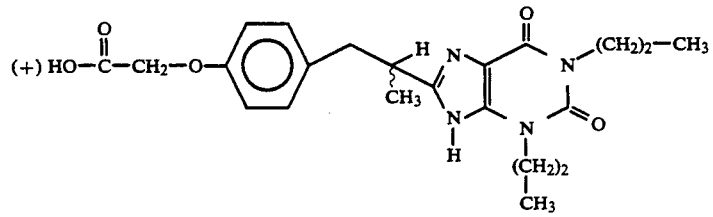

Dissolve 4-[[2-(1,1-dimethylethoxy)-2-oxoethyl]oxy]-alpha-methyl-benzenepropanoic acid, methyl ester (15.0 g, 48.6 mmol) in ethyl ether (50 mL) and adsorb onto silica gel (45 g). Evaporate the solvent under a stream of nitrogen and add pH 7 phosphate buffer (1500 mL of a 0.1M solution) followed by lipase P-30 (15 g). Maintain a ph of 7 by the addition of 1M sodium hydroxide. Stir for 24 hours, filter through silica gel and rinse the filter cake with chloroform (500 mL). Separate the aqueous phase and extract with chloroform (4×300 mL). Dry (MgSO4) the combined organic phases and evaporate the solvent in vacuo. Purify by flash chromatography (10% methanol/chloroform) to give (−)-4-[[2-(1,1-dimethylethoxy)-2-oxoethyl]oxy]-alpha-methyl-benzenepropanoic acid, methyl ester (6.43 g, 91% ee) and (+)-4-[[2-(1,1-dimethylethoxy)-2-oxoethyl]oxy]-alpha-methyl-benzenepropanoic acid (6.59 g, 90% ee after reesterification with diazomethane).

Dissolve (+)-4-[[2-(1,1-dimethylethoxy)-2-oxoethyl]oxy]-alpha-methyl-benzenepropanoic acid (90% ee) (6.04 g, 20.5 mmol) in ethyl ether (400 mL) and treat with excess diazomethane. Wash with saturated sodium hydrogen carbonate (2×300 mL) and brine (300 mL). Dry (MgSO4) and evaporate the solvent in vacuo to give (+)-4-[[2-(1,1-dimethylethoxy)-2-oxoethyl]oxy]-alpha-methyl-benzenepropanoic acid, methyl ester (5.85 g).

Dissolve (+)-4-[[2-(1,1-dimethylethoxy)-2-oxoethyl]oxy]-alpha-methyl-benzenepropanoic acid, methyl ester (5.74 g, 18.6 mmol) in ethyl ether and adsorb onto silica gel (18 g). Evaporate the solvent in vacuo to leave a white powder. Suspend the powder in pH 7 phosphate buffer (600 mL of a 0.1M solution). Add lipase P-30 (5.74 g) and stir for 16 hours. Filter and extract with ethyl ether (3×400 mL). Dry (MgSO4), evaporate the solvent in vacuo and purify by flash chromatography (5→10% methanol/chloroform) to give the title compound (5.09 g, 98% ee after reesterification with diazomethane); $[\alpha]_d^{20} = +18.9°$ (C=0.97, CHCl3).

Scheme A, step h:
(+)-2-[[4-[3-[(6-Amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester Dissolve (+)-4-[[2-(1,1-dimethylethoxy)-2-oxoethyl]oxy]-alpha-methyl-benzenepropanoic acid (3.02 g, 10.27 mmol) in tetrahydrofuran (100 mL) and treat with N-methylmorpholine (1.2 mL, 10.27 mmol). Cool to −20° C., add isobutyl chloroformate (1.35 mL, 10.27 mmol) and stir for 1 hour. Add a solution of 1,3-dipropyl-5,6-diaminouracil (2.33 g, 10.27 mmol) in dimethylformamide (8 mL) and stir for 6 hours at −20° C. Warm to room temperature and dilute with chloroform (600 mL). Wash with saturated sodium hydrogen carbonate (300 mL), then brine (3×300 mL). Dry (MgSO4) and evaporate the solvent in vacuo. Purify by flash chromatography (5→10→15→20% isopropanyl/hexane) to give the title compound as a foam (3.74 g, 72%); $[\alpha]_d^{20} = +51.4°$ (C=1.03, CHCl3).

Scheme A, step i:
(+)-2-[4-[2-(2,3,6,9-Tetrahydro-1,3-dipropyl-2,6-dioxo-1H-purin-8-yl)propyl]phenoxy]acetic acid Dissolve (+)-2-[[4-[3-[(6-amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester (2.20 g, 4.38 mmol) in benzene (100 mL) and treat with triethyloxonium tetrafluoroborate (35 mL of a 1M solution in methylene chloride, 35.02 mmol) and place under a nitrogen atmosphere. Heat at 40° C. for 24 hours, cool and dilute with phosphate buffer (400 mL). Extract into ethyl ether (3×300 mL), dry (MgSO4) and evaporate the solvent in vacuo. Purify by radial chromatography (2→4% methanol chloroform) to give the ethyl enolate of (+)-2-[[4-[3-[(6-amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester (0.85 g); $[\alpha]_d^{20} = +67.5°$ (C=0.80, CHCl3).

Dissolve the ethyl enolate of (+)-2-[[4-[3-[(6-amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester (0.68 g, 1.28 mmol) in benzene (200 mL) and heat at 70° C. for 20 hours. Evaporate the solvent in vacuo and purify the residue by radial chromatography (30→40→50% ethyl acetate/hexane) to give (+)-2-[4-[2-(2,3,6,9-tetrahydro-1,3-dipropyl-2,6-dioxo-1H-purin-8-yl)propyl]phenoxy]acetic acid, ethyl ester (0.55 g); $[\alpha]_d^{20} = +54.5°$ (C=0.88, CHCl3).

Dissolve (+)-2-[4-[2-(2,3,6,9-tetrahydro-1,3-dipropyl 2,6-dioxo-1H-purin-8-yl)propyl]phenoxy]acetic acid, ethyl ester (0.49 g, 1.07 mmol) in ethanol (10 mL) and treat with a solution of potassium hydroxide (0.072 g, 1.29 mmol) in water (10 mL). Stir for 3 hours, then dilute with water (200 mL) and acidify with 10% hydrochloric acid. Extract into chloroform (2×400 mL), then ether (400 mL) and dry (MgSO4). Evaporate the solvent in vacuo to give the title compound as a white solid (0.33 g, 72%); [α]$_d$ $^{20}$= +81° (C=0.069, DMSO).

EXAMPLE 14

Preparation of
(−)-2-[4-[2-(2,3,6,9-Tetrahydro-1,3-dipropyl-2,6-dioxo-1H-purin-8-yl)propyl]phenoxy]acetic acid Scheme A, step g:
(−)-4-[[2-(1,1-Dimethylethoxy)-2-oxoethyl]oxy]-alpha-methyl-benzenepropanoic acid

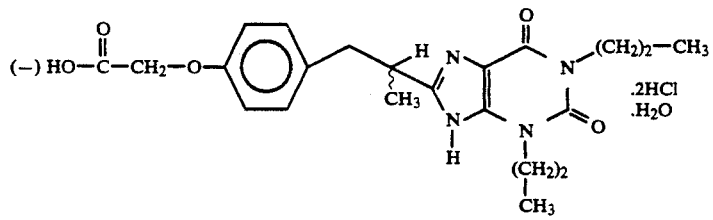

Dissolve 4-[[2-(1,1-dimethylethoxy)-2-oxoethyl]oxy]-alpha-methyl-benzenepropanoic acid, methyl ester (91% ee) (6.43 g, 20.9 mmol) in ethyl ether and adsorb onto silica gel (19.5 g). Evaporate the solvent to leave a white powder. Add pH 7 phosphate buffer (650 mL of a 0.1M solution) followed by lipase P-30 (0.64 g). Stir for 6.5 hours then add additional lipase P-30 (5.5 g). Stir for 2 hours, dilute with brine (400 mL) and extract into chloroform (4×400 mL). Combine the organic phases, wash with saturated sodium hydrogen carbonate (400 mL) and dry (MgSO4 then Na2SO4). Evaporate the solvent in vacuo to give (−)-4-[[2-(1,1-dimethylethoxy)-2-oxoethyl]oxy]-alpha-methyl-benzenepropanoic acid, methyl ester (3.94 g, 98% ee).

Suspend lithium hydride (430 mg, 54.3 mmol) in hexamethylphosphoramide (40 mL) and treat with 1-propanethiol (5.04 mL, 54.3 mmol). Add a solution of (−)-4-[[2-(1,1-dimethylethoxy)-2-oxoethyl]oxy]-alpha-methyl-benzenepropanoic acid, methyl ester (2.39 g, 7.75 mmol) in hexamethylphosphoramide (40 mL). Stir for 48 hours and pour into ice cold 5% hydrochloric acid [300 mL]. Separate the aqueous phase, extract with ethyl ether (4×300 mL), wash with water and dry (Na2SO4). Evaporate the solvent in vacuo and purify by flash chromatography (5→10% methanol/chloroform) followed by radial chromatography (3→5% methanol/chloroform) to give the title compound (1.78 g); [α]$_d$ $^{20}$= −17.3° (C=1.25, CHCl3).

Scheme A, step h:
(−)-2-[[4-[3-[(6-Amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester Dissolve (−)-4-[[2-(1,1-dimethylethoxy)-2-oxoethyl]oxy]-alpha-methyl-benzenepropanoic acid (1.92 g, 6.52 mmol) in tetrahydrofuran (50 mL) and treat with N-methylmorpholine (0.77 mL, 6.52 mmol). Cool to −20° C. and treat with isobutyl chloroformate (0.86 mL, 6.52 mmol). Stir for 1 hour and add a solution of 1,3-dipropyl-5,6-diaminouracil (1.48 g, 6.52 mmol) in dimethylformamide (4 mL). Stir at −20° C. for 3 hours and warm to room temperature. Stir for 2 hours and dilute with chloroform (400 mL). Separate the organic phase and wash with saturated sodium hydrogen carbonate (300 mL), then brine (2×400 mL). Dry (Na2SO4) and evaporate the solvent in vacuo to give 4.31 g crude product. Purify by flash chromatography (10→15→20% isopropanol/hexane) to give the title compound (2.16 g, 66%); [α]$_d$ $^{20}$= −45.8° (C=1.00, CHCl3).

Scheme A, step i:
(−)-2-[4-[2-(2,3,6,9-Tetrahydro-1,3-dipropyl-2,6-dioxo-1H-purin-8-yl)propyl]phenoxy]acetic acid Dissolve (−)-2-[[4-[3-[(6-amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester (1.76 g, 3.50 mmol) in benzene (500 mL) and treat with triethyloxonium tetrefluoroborate (28 mL of a 1M solution in methylene chloride, 28 mmol) and heat at 50° C. for 20 hours. Cool, dilute with ethyl ether (300 mL) and wash with phosphate buffer (500 mL). Dry (MgSO4) and evaporate the solvent in vacuo. Purify by radial chromatography (2→4% methanol/chloroform) to give the ethyl enolate of (−)-2-[[4-[3-[(6-amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester (1.14 mg, 61%); [α]$_d$ $^{20}$= −64.1° (C=1.16, CHCl3).

Dissolve the ethyl enolate of (−)-2-[[4-[3-[(6-amino-1-propyl-1,2,3,4-tetrahydro-3-propyl-2,4-dioxo-5-pyrimidinyl)amino]-2-methyl-3-oxopropyl]phenyl]oxy]-acetic acid, 1,1-dimethylethyl ester (1.01 g, 1.9 mmol) in anhydrous benzene (200 mL) and heat at 80° C. for 24 hours. Evaporate the solvent in vacuo and purify the residue by radial chromatography (40→50% ethyl acetate/hexane) to give (−)-2-[4-[2-(2,3,6,9-tetrahydro-1,3-dipropyl-2,6-dioxo-1H-purin-8-yl)propyl]phenoxy]acetic acid, ethyl ester (0.7 g, 81%); [α]$_d$ $^{20}$= −54.3° (C=0.856, CHCl3).

Dissolve (−)-2-[4-[2-(2,3,6,9-tetrahydro-1,3-dipropyl-2,6-dioxo-1H-purin-8-yl)propyl]phenoxy]acetic acid, ethyl ester (0.62 g, 1.36 mmol) in ethanol (15 mL) and treat with a solution of potassium hydroxide (0.091 g, 1.63 mmol) in water (15 mL). Stir for 3 hours, add water (200 mL) and wash with ethyl ether (300 mL). Acidify the aqueous phase with 10% hydrochloric acid and extract into chloroform (4×150 mL). Dry (MgSO4) and evaporate the solvent in vacuo to give the title compound (0.47 g, 81%); [α]$_d$ $^{20}$= −79.1° (C=0.537, DMSO).

The following compounds can be prepared by procedures analogous to those described in Examples 1-14:
2-[4-[2-(2,3,6,9-Tetrahydro-1,3-dipropyl-2,6-dioxo-1H-purin-8-yl)propyl]phenoxy]propionic acid;
2-[4-[2-(2,3,6,9-Tetrahydro-1,3-dipropyl-2,6-dioxo-1H-purin-8-yl)propyl]phenylthio]propionic acid;
2-[4-[2-(2,3,6,9-Tetrahydro-1,3-dipropyl-2,6-dioxo-1H-purin-8-yl)propyl]phenylamino]propionic acid.

The compounds of formula (II) can be prepared by techniques and procedures well known and appreciated by one of ordinary skill in the art. A general synthetic procedure for the preparation of compounds of formula (II) is set forth in Scheme C. In Scheme C, all substituents, unless otherwise indicated, are as previously defined.

[[2,3,6,9-tetrahydro-1,3-dialkyl-2,6-dioxo-1H-purin-8-yl]alkyl]phenylhetero-N-(2-aminoethyl)alkanamide peptide of structure (19). The [[2,3,6,9-tetrahydro-1,3-dialkyl-2,6-dioxo-1H-purin-8-yl]alkyl]phenylhetero-N-

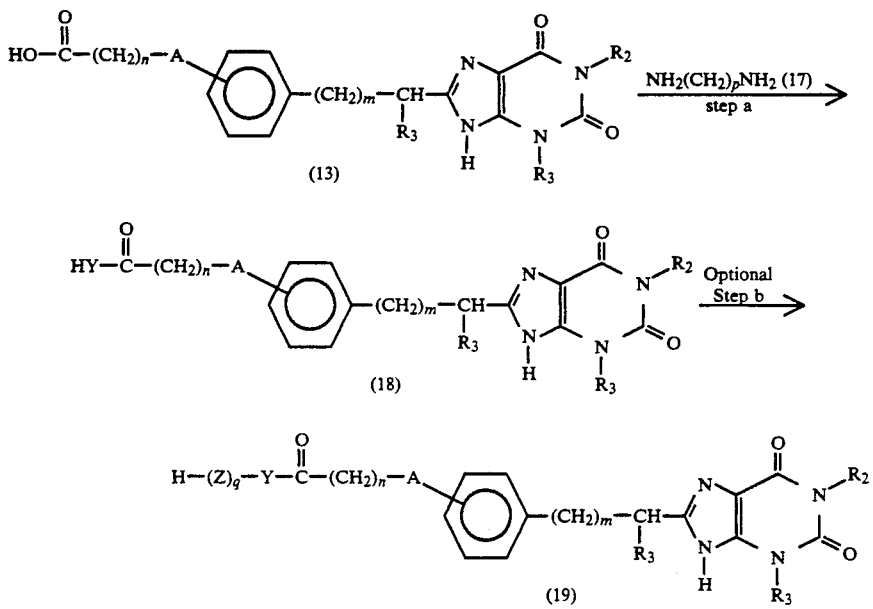

Scheme C provides a general synthetic procedure for the preparation of compounds of formula (II).

In step a, the [[2,3,6,9-tetrahydro-1,3-dialkyl-2,6-dioxo-1H-purin-8-yl]alkyl]phenylhetero alkanoic acid of structure (13) is amidated with amine of structure (17) to give the [[2,3,6,9-tetrahydro-1,3-dialkyl-2,6-dioxo-1H-purin-8-yl]alkyl]phenylhetero-N-(2-aminoethyl)alkanamide of structure (18). The [[2,3,6,9-tetrahydro-1,3-dialkyl-2,6-dioxo-1H-purin-8-yl]alkyl]phenylhetero alkanoic acid of structure (13) is typically contacted with an equimolar amount of an activating agent, such as N-hydroxysuccinimide and a molar excess of coupling agent, such as 1-(3-dimethylaminopropyl)-3-ethylcarbodiimide hydrochloride. The reactants are typically contacted in an organic solvent such as dimethylformamide. The reactants are typically stirred together for a period of time ranging from 30 minutes to 5 hours and at a temperature range of from 0° C. to room temperature. A molar excess of amine of structure (17) is then added and the reactants stirred together for a period of time ranging from 30 minutes to 24 hours and at a temperature range of from 0° C. to reflux. The [[2,3,6,9-tetrahydro-1,3-dialkyl-2,6-dioxo-1H-purin-8-yl]alkyl]-phenylhetero-N-(2-aminoethyl)alkanamide of structure (18) is recovered from the reaction zone by extractive methods as is known in the art and purified by silica gel chromatography.

In optional step b, the [[2,3,6,9-tetrahydro-1,3-dialkyl-2,6-dioxo-1H-purin-8-yl]alkyl]phenylhetero-N-(2-aminoethyl)alkanamide of structure (18) is amidated with an appropriate amino acid or peptide to give the (2-aminoethyl)alkanamide of structure (18) is typically contacted with a molar deficiency of a suitably N-protected amino acid or peptide, a molar excess of a additive such as hydroxybenzotriazole, a molar excess of a coupling agent, such as 1-(3-dimethylaminopropyl)-3-ethylcarbodiimide hydrochloride and a non-nucleophilic base, such as diisopropylethylamine. The reactants are typically stirred together for a period of time ranging from 1-24 hours and at a temperature range of from 10° C. to room temperature. The protected [[2,3,6,9-tetrahydro-1,3-dialkyl-2,6-dioxo-1H-purin-8-yl]alkyl]phenylhetero-N-(2-aminoethyl)alkanamide peptide of structure (19) is recovered from the reaction zone by extractive methods as is known in the art.

The protected [[2,3,6,9-tetrahydro-1,3-dialkyl-2,6-dioxo-1H-purin-8-yl]alkyl]phenylhetero-N-(2-aminoethyl)alkanamide peptide of structure (19) is then deprotected to give the [[2,3,6,9-tetrahydro-1,3-dialkyl-2,6-dioxo-1H-purin-8-yl]alkyl]phenylhetero-N-(2-aminoethyl)alkanamide peptide of structure (19).

The selection, utilization and subsequent deprotection of suitable amino acid and peptide amino protecting groups are well known to one of ordinary skill in the art and are described in "Peptide Synthesis' Miklos Bodanszky, Wiley (1966).

The following examples present typical syntheses as described in Scheme C. These examples are illustrative only and are not intended to limit the scope of the present invention in any way.

EXAMPLE 15

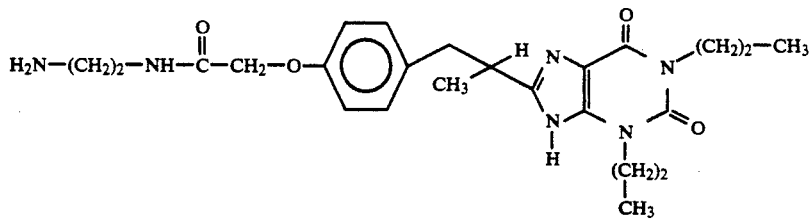

Preparation of N-(2-Aminoethyl)-2-[4-[2-(2,3,6,9-tetrahydro-1,3-dipropyl-2,6-dioxo-1H-purin-8-yl)propyl]phenoxy]-acetamide Dissolve 2-[4-[2-(2,3,6,9-tetrahydro-1,3-dipropyl-2,6-dioxo-1H-purin-8-yl)propyl]phenoxy]acetic acid (800 mg, 1.87 mmol) in dimethylformamide (20 mL) and treat with N-hydroxysuccinimide (215 mg, 1.87 mmol) and 1-(3-dimethylaminopropyl)-3-ethylcarbodiimide hydrochloride (751 mg, 3.92 mmol). Stir for 1 hour and add to a stirring solution of ethylenediamine (20 mL of a 10% solution in methanol). Stir for 1 hour and dilute with chloroform (600 mL). Separate the organic phase, wash with 5% sodium carbonate (200 mL), then brine (300 mL). Dry (MgSO$_4$) and evaporate the solvent in vacuo. Purify by radial chromatography (5→10% methanol/chloroform with 1% ammonium hydroxide) and recrystallize (10% isopropanol/hexane) to give the title compound (364 mg); mp 143–44° C.

EXAMPLE 16

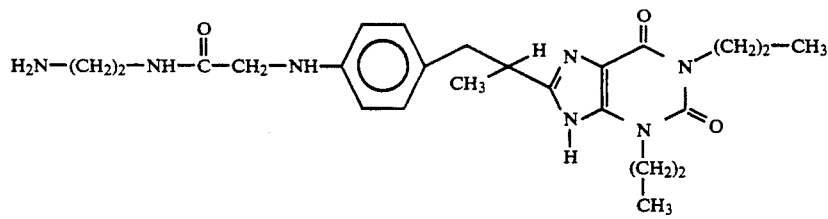

Preparation of N-(2-Aminoethyl)-2-[4-[2-(2,3,6,9-tetrahydro-1,3-dipropyl-2,6-dioxo-1H-purin 8-yl)propyl]phenylamino]-acetamide Dissolve 2-[4-[2-(2,3,6,9-tetrahydro-1,3-dipropyl-2,6-dioxo-1H-purin-8-yl)propyl]phenylamino]acetic acid (754 mg, 1.87 mmol) in dimethylformamide (20 mL) and treat with N-hydroxysuccinimide (215 mg, 1.87 mmol) and 1-(3-dimethylaminopropyl)-3-ethylcarbodiimide hydrochloride (751 mg, 3.92 mmol). Stir for 1 hour and add to a stirring solution of ethylenediamine (20 mL of a 10% solution in methanol). Stir for 1 hour and dilute with chloroform (600 mL). Separate the organic phase, wash with 5% sodium carbonate (200 mL), then brine (300 mL). Dry (MgSO$_4$) and evaporate the solvent in vacuo. Purify by radial chromatography to give the title compound.

EXAMPLE 17

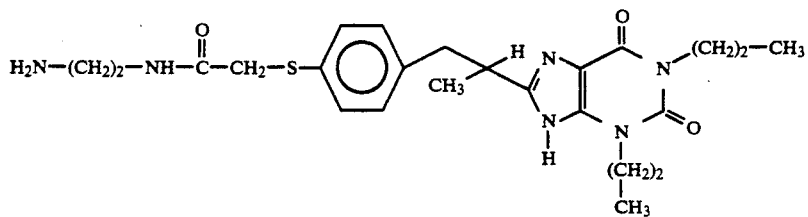

Preparation of N-(2-Aminoethyl)-2-[4-[2-(2,3,6,9-tetrahydro-1,3-dipropyl-2,6-dioxo-1H-purin-8-yl)propyl]phenylthio]-acetamide Dissolve 2-[4-[2-(2,3,6,9-tetrahydro-1,3-dipropyl-2,6-dioxo-1H-purin-8-yl)propyl]phenylthio]acetic acid (785 mg, 1.87 mmol) in dimethylformamide (20 mL) and treat with N-hydroxysuccinimide (215 mg, 1.87 mmol) and 1-(3-dimethylaminopropyl)-3-ethylcarbodiimide hydrochloride (751 mg, 3.92 mmol). Stir for 1 hour and add to a stirring solution of ethylenediamine (20 mL of a 10% solution in methanol). Stir for 1 hour and dilute with chloroform (600 mL). Separate the organic phase, wash with 5% sodium carbonate (200 mL), then brine (300 mL). Dry (MgSO$_4$) and evaporate the solvent in vacuo. Purify by radial chromatography to give the title compound.

EXAMPLE 18

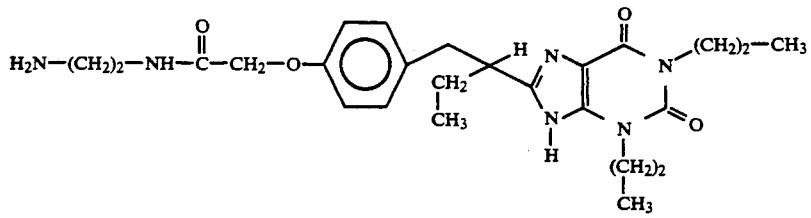

Preparation of N-(2Aminoethyl)-2-[4-[1-(2,3,6,9-tetrahydro-1,3-dipropyl-2,6-dioxo-1H-purin-8-yl)propyl]phenoxy]-acetamide Dissolve 2-[4-[1-(2,3,6,9-tetrahydro-1,3-dipropyl-2,6-dioxo-1H-purin-8-yl)propyl]phenoxy]acetic acid (720 mg, 1.68 mmol) in dimethylformamide (10 mL) and treat with N-hydroxysuccinimide (192 mg, 1.68 mmol) and 1-(3-dimethylaminopropyl)-3-ethylcarbodiimide hydrochloride (676 mg, 3.53 mmol). Stir for 1.5 hours and add to a solution of ethylenediamine (10 mL of a 10% solution in methanol). Stir for 1.5 hours, pour into brine (300 mL) and extract with ethyl acetate (3×200 mL) and chloroform (3×300 mL). Dry (MgSO4) and evaporate the solvent in vacuo. Purify by radial chromatography (5→10→20% methanol chloroform with 1% ammonium hydroxide) and recrystallize (10% isopropanol/pentane to give the title compound (51 mg) as a white solid; mp 139–40° C.

EXAMPLE 19

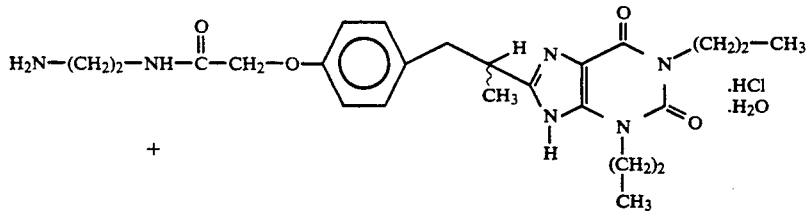 + 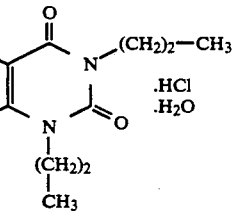

Preparation of (+)-N (2-Aminoethyl)-2-[4-[2-(2,3,6,9-tetrahydro-1,3-dipropyl-2,6-dioxo-1H-purin-8-yl)propyl]phenoxy]-acetamide Dissolve (+)-2-[4-[2-(2,3,6,9-tetrahydro-1,3-dipropyl-2,6-dioxo-1H-purin-8-yl)propyl]phenoxy]acetic acid (0.28 g, 0.65 mmol) in dimethylformamide (10 mL) and treat with N-hydroxysuccinimide (0.074 g, 0.65 mmol) and 1-(3-dimethylaminopropyl)-3-ethylcarbodiimide hydrochloride (0.262 g, 1.37 mmol). Stir for 1 hour and add a solution of ethylenediamine (10 mL of a 10% solution in methanol) and stir for 1 hour. Dilute with chloroform (500 mL), wash with 5% sodium carbonate (200 mL) and dry (MgSO4). Evaporate the solvent in vacuo and purify by radial chromatography (10→20% methanol/chloroform with 1% ammonium hydroxide). Dissolve the purified material in 5% methanol/ethyl ether and treat with ethereal hydrochloric acid. Evaporate the solvent in vacuo and triturate the residue with ethyl ether. Filter the resulting solid and dry to give the title compound (88 mg); $[\alpha]_d^{20} = +75.7°$ (C=0.96, H2O).

Anal. Calcd for $C_{24}H_{34}N_6O_4 \cdot HCl \cdot H_2O$: C, 54.90; H, 7.10; N, 16.01; Found: C, 55.31; H, 7.47; N, 15.76.

EXAMPLE 20

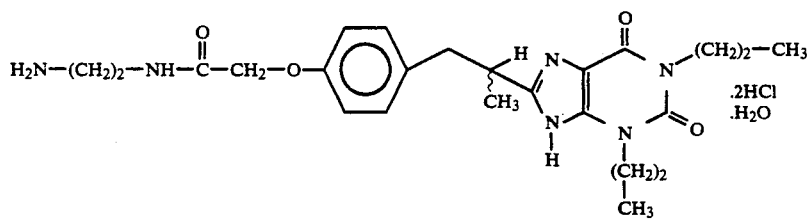

Preparation of (−)-N-(2-Aminoethyl)-2-[4-[2-(2,3,6,9-tetrahydro-1,3-dipropyl-2,6-dioxo-1H-purin-8-yl)propyl]phenoxy]-acetamide Dissolve (−)-2-[4-[2-(2,3,6,9-tetrahydro-1,3-dipropyl-2,6-dioxo-1H-purin-8-yl)propyl]phenoxy]acetic acid (0.45 g, 1.05 mmol) in dimethylformamide (20 mL) and treat with N-hydroxysuccinimide (0.12 g, 1.05 mmol) and 1-(3-dimethylaminopropyl)-3-ethylcarbodiimide hydrochloride (0.42 g, 2.20 mmol). Stir for 85 minutes and add to a solution of ethylenediamine (10% in methanol). Stir for 26 hours and dilute with chloroform (500 mL). Separate the organic phase and wash with 5% sodium carbonate, then brine (400 mL). Dry (MgSO4) and evaporate the solvent in vacuo. Purify by radial chromatography (10→20% methanol/chloroform with 1% ammonium hydroxide) to give an oil (370 mg). Dissolve the oil in ethyl ether, treat with ethereal hydrochloric acid and evaporate the solvent in vacuo. Triturate the residue with ethyl ether, filter and dry to give the title compound (361 mg); $[\alpha]_d^{20} = -80.8°$ (C=0.95, H2O).

Anal. Calcd for $C_{24}H_{34}N_6O_4 \cdot 2HCl \cdot H_2O$: C, 51.34; H, 6.82; N, 14.97; Found: C, 51.74; H, 6.69; N, 14.83.

EXAMPLE 21

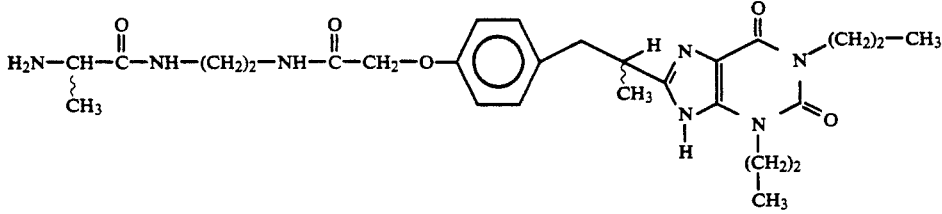

Preparation of 2-Amino-N-[2-[[1-oxo-3-[[4-[2-(2,3,6,9-tetrahydro-1,3-dipropyl-2,6-dioxo-1H-purin-8-yl)propyl]phenyl]oxy]ethyl ]amino]ethyl-propanamide Mix (−)-N-(2-aminoethyl)-2-[4-[2-(2,3,6,9-tetrahydro-1,3-dipropyl-2,6-dioxo-1H-purin-8-yl)propyl]-phenoxy]-acetamide (4.70 g, 10 mmol), N-t-butyloxycarbonyl-L-alanine (1.0 g, 5.3 mmol), hydroxybenztriazole (1.65 g, 11 mmol) and 1-(3-dimethylaminopropyl)-3-ethylcarbodiimide hydrochloride (2.1 g, 11 mmol). Add a solution of diisopropylethylamine (3.8 mL) in methylene chloride (20 mL) and stir at room temperature for several hours. Dilute with ethyl acetate (150 mL), wash with cold 0.5N hydrochloric acid, saturated aqueous sodium hydrogen carbonate and brine. Dry (MgSO₄) and evaporate the solvent in vacuo to give 2-(t-butyloxycarbonylamino)-N-[2-[[1-oxo-3-[[4-[2-(2,3,6,9-tetrahydro-1,3-dipropyl-2,6-dioxo-1H-purin-8-yl)propyl]phenyl]oxy]ethyl]amino]ethyl-propanamide.

Dissolve 2-(t-butyloxycarbonylamino)-N-[2-[[1-oxo-3-[[4-[2-(2,3,6,9-tetrahydro-1,3-dipropyl-2,6-dioxo-1H-purin-8-yl)propyl]phenyl]oxy]ethyl]amino]ethyl-propanamide (6.41 g, 10 mmol) in 4N hydrochloric acid in dioxane (25 mL, 100 mmol) and stir for 30 minutes. Evaporate the solvent in vacuo and purify by ion-exchange chromatography to give the title compound.

The following compounds can be prepared analogously to those described in Examples 15–21:

N-(3-Aminopropyl)-2-[4-[2-(2,3,6,9-tetrahydro-1,3-dipropyl-2,6-dioxo-1H-purin-8-yl)propyl]phenoxy]-acetamide;
N-(3-Aminopropyl)-2-[4-[2-(2,3,6,9-tetrahydro-1,3-dipropyl-2,6-dioxo-1H-purin-8-yl)propyl]phenylthio]-acetamide;
N-(3-Aminopropyl)-2-[4-[2-(2,3,6,9-tetrahydro-1,3-dipropyl-2,6-dioxo-1H-purin-8-yl)propyl]phenylamino]-acetamide;
N-(3-Aminopropyl)-2-[4-[2-(2,3,6,9-tetrahydro-1,3-dipropyl-2,6-dioxo-1H-purin-8-yl)propyl]phenoxy]-propionamide;
N-(3-Aminopropyl)-2-[4-[2-(2,3,6,9-tetrahydro-1,3-dipropyl-2,6-dioxo-1H-purin-8-yl)propyl]phenylthio]-propionamide;
N-(3-Aminopropyl)-2-[4-[2-(2,3,6,9-tetrahydro-1,3-dipropyl-2,6-dioxo-1H-purin-8-yl)propyl]phenylamino]-propionamide.

The compounds of formula (III) can be prepared using techniques and procedures well known and appreciated by one of ordinary skill in the art. A general synthetic procedure for the preparation of compounds of formula (III) is set forth in Scheme D. In Scheme D, all substituents, unless otherwise indicated, are as previously defined.

Scheme D

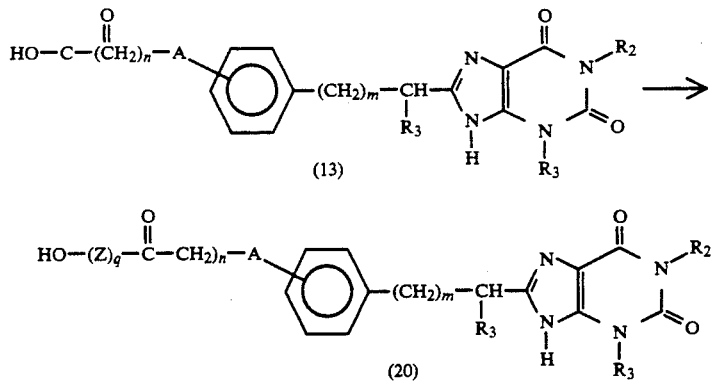

Scheme D provides a general synthetic procedure for the preparation of compounds of formula (III).

An appropriate [[2,3,6,9-tetrahydro-1,3-dialkyl-2,6-dioxo-1H-purin-8-yl]alkyl]phenylhetero alkanoic acid of structure (13) is amidated with a suitable carboxylate protected amino acid or peptide to give the [[2,3,6,9-tetrahydro-1,3-dialkyl-2,6-dioxo-1H-purin-8-yl]alkyl]-phenylhetero alkanamide peptide of structure (20) after deprotection as described previously in Scheme C.

Starting materials for use in the general synthetic procedure outlined in Scheme D are readily available to one of ordinary skill in the art.

The following examples present typical syntheses as described by Scheme D. These examples are understood to be illustrative only and are not intended to limit the scope of the invention in any way.

EXAMPLE 22

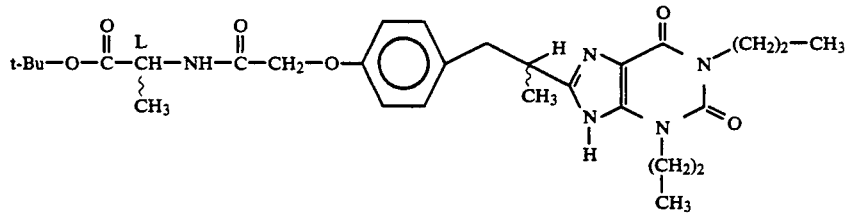

Preparation of
(−)-N-[[[4-[2-(2,3,6,9-Tetrahydro-1,3-dipropyl-2,6-dioxo-1H-purin-8-yl)propyl]phenyl]oxy]acetyl]-L-alanine, t-butyl ester Mix (−)-2-[4-[2-(2,3,6,9-tetrahydro-1,3-dipropyl-2,6-dioxo-1H-purin-8-yl)propyl]phenoxy]acetic acid (4.28 g, 10 mmol), L-alanine t-butylester hydrochloride (965 mg, 5.3 mmol), hydroxybenztriazole (1.65 g, 11 mmol) and 1-(3-dimethylaminopropyl)-3-ethylcarbodiimide hydrochloride (2.1 g, 11 mmol). Add a solution of diisopropylethylamine (3.8 mL) in methylene chloride (20 mL) and stir at room temperature for several hours. Dilute with ethyl acetate (150 mL), wash with cold 0.5N hydrochloric acid, saturated aqueous sodium hydrogen carbonate and brine. Dry (MgSO₄) and evaporate the solvent in vacuo to give the title compound.

EXAMPLE 23

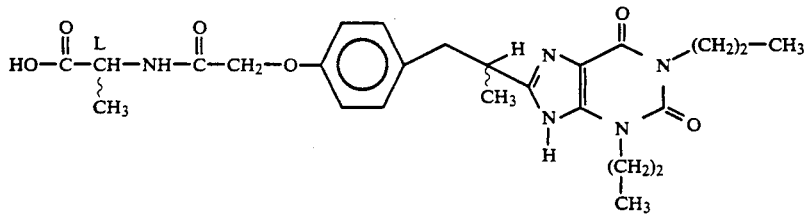

Preparation of
(−)-N-[[[4-[2-(2,3,6,9-Tetrahydro-1,3-dipropyl-2,6-dioxo-1H-purin-8-yl)propyl]phenyl]oxy]acetyl]-L-alanine Dissolve (−)-N-[[[4-[2-(2,3,6,9-tetrahydro-1,3-dipropyl-2,6-dioxo-1H-purin-8-yl)propyl]phenyl]oxy]acetyl]-L-alanine, t-butyl ester (5.55 g, 10 mmol) in 4N hydrochloric acid in dioxane (25 mL, 100 mmol) and stir for several hours. Evaporate the solvent in vacuo and purify by ion-exchange chromatography to give the title compound.

The following compounds can be prepared by procedures analogous to those described for Examples 22-23:
N-[[[4-[2-(2,3,6,9-Tetrahydro-1,3-dipropyl-2,6-dioxo-1H-purin-8-yl)propyl]phenyl]oxy]acetyl]-L-arginine;
N-[[[4-[2-(2,3,6,9-Tetrahydro-1,3-dipropyl-2,6-dioxo-1H-purin-8-yl)propyl]phenyl]oxy]acetyl]-L-leucine.

In a further embodiment, the present invention provides a method of providing a selective $A_1$-adenosine receptor antagonist effect in a patient in need thereof comprising administering to said patient a therapeutically effective $A_1$-antagonistic amount of a compound of formula (I), (II) or (III).

A selective $A_1$-adenosine receptor antagonist effect refers to a selective antagonism of $A_1$-mediated effects of adenosine relative to $A_1$-agonist and $A_2$-mediated effects. Although the compounds of the present invention may also express some measurable $A_1$-agonist, $A_2$-agonist or $A_2$-antagonist activity, the $A_1$-antagonist activity is the primary and the physiologically significant effect of these compounds. For example, a compound having both $A_1$ and $A_2$ antagonist activity will be active as an $A_1$-antagonist at much lower concentrations than as an $A_2$-antagonist and will have a relatively high $A_2/A_1$ activity ratio.

As used herein, the term "patient" refers to warm-blooded animals or mammals, including mice, rats and humans. A patient is in need of a selective $A_1$-adenosine receptor antagonist effect when the patient is in need of relief from an $A_1$-mediated response such as the antilipolytic, cardiac depressant and CNS depressant effects of adenosine. A selective $A_1$ antagonist would thus provide a lipolytic, cardiac stimulant and CNS stimulant effect by blocking the naturally occurring $A_1$-adenosine receptor mediated effects of adenosine.

For example, administration of an $A_1$-adenosine receptor antagonist to a patient suffering from Alzheimer's Disease would result in providing a cognition enhancement effect. Furthermore, administration of an $A_1$-adenosine receptor antagonist to a patient suffering from congestive heart failure would result in providing a cardiotonic or inotropic effect. Also, administration of an $A_1$-adenosine receptor antagonist to a patient suffering from pulmonary bronchoconstriction would result in providing a bronchodilating effect.

Successful treatment of a patient with a compound of the present invention is understood to provide a selective $A_1$ antagonist effect resulting in reducing or eliminating the $A_1$-mediated effects of adenosine without significantly affecting $A_2$-mediated effects.

The identification of those patients who are in need of treatment to provide an $A_1$ antagonist effect is well within the ability and knowledge of one skilled in the art. A clinician skilled in the art can readily identify, by the use of clinical tests, physical examination and medical/family history, those patients who are in need of an $A_1$ antagonist effect. For example, patients suffering from congestive heart failure, Alzheimer's disease or pulmonary bronchoconstriction are in need of treatment to provide an $A_1$ antagonist effect.

A therapeutically effective $A_1$-antagonistic amount of a compound of formula (I), (II) or (III) is an amount which is effective in selectively reducing or eliminating the $A_1$-mediated response to adenosine and in thus antagonizing the $A_1$-mediated antilipolytic, cardiac depressant and CNS depressant effects of adenosine.

A therapeutically effective $A_1$-antagonistic dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

A therapeutically effective $A_1$-antagonistic amount of a compound of formula (I), (II) or (III) will generally vary from about 0.5 milligram per kilogram of body weight per day (mg/kg/day) to about 500 mg/kg/day. A daily dose of from about 5 mg/kg to about 50 mg/kg is preferred.

In effecting treatment of a patient, compounds of formula (I), (II) or (III) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Compounds of formula (I), (II) or (III) can be administered in the form of pharmaceutical compositions or medicaments which are made by combining the compounds of formula (I), (II) or (III) with pharmaceutically acceptable carriers or excipients, the proportion and nature of which are determined by the chosen route of administration, and standard pharmaceutical practice.

In another embodiment, the present invention provides compositions comprising a compound of formula (I), (II) or (III) in admixture or otherwise in association with one or more inert carriers. These compositions are useful, for example, as assay standards, as convenient means of making bulk shipments, or as pharmaceutical compositions. An assayable amount of a compound of formula (I), (II) or (III) is an amount which is readily measurable by standard assay procedures and techniques as are well known and appreciated by those skilled in the art. Assayable amounts of a compound of formula (I), (II) or (III) will generally vary from about 0.001% to about 75% of the composition by weight. Inert carriers can be any material which does not degrade or otherwise covalently react with a compound of formula (I), (II) or (III). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of formula (I), (II) or (III) in admixture or otherwise in association with one or more pharmaceutically acceptable carriers or excipients.

The pharmaceutical compositions or medicaments are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of formula (1) may be incorporated with excipients and used in the form of tablets, troches, capsules, elixirs, suspensions, syrups, wafers, chewing gums and the like. These preparations should contain at least 4% of the compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of formula (I), (II) or (III) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

It is, of course, understood that the compounds of formula (I), (II) and (III) may exist in a variety of isomeric configurations including structural as well as stereo isomers. It is further understood that the present invention encompasses those compounds of formula (I), (II) and (III) in each of their various structural and stereo isomeric configurations as individual isomers and as mixtures of isomers. For example, it is readily evident that the carbon atom bearing $R_3$ is a chiral carbon atom which can be present in the R or S configuration. The present invention is specifically understood to include compounds of formula (I), (II) and (III) in which this $R_3$-bearing carbon is in the R or the S configuration, as well as racemic mixtures thereof. Other chiral centers may also be present in the compounds of the present invention.

As with any group of structurally related compounds which possess a particular generic utility, certain groups and configurations are preferred for compounds of formula (I), (II) or (III) in their end-use application. The compounds of formula (I) wherein $R_1$ and $R_2$ are n-propyl, $R_3$ is methyl or ethyl, m is 0 or 1, A is oxygen, n is 1, and $R_4$ is H are generally preferred. The compounds of formula (II) wherein $R_1$ and $R_2$ are n-propyl, $R_3$ is methyl or ethyl, m is 0 or 1, A is oxygen, n is 1, Y is —NHCH$_2$CH$_2$NH—, and q is 0 are generally preferred. The compounds of formula (III) wherein $R_1$ and $R_2$ are n-propyl, $R_3$ is methyl or ethyl, m is 0 or 1, A is oxygen, n is 1, and Z is $$-NH-CH-\underset{\underset{(CH_2)_4NH_2}{|}}{\overset{\overset{O}{\|}}{C}}-$$

are generally preferred. Compounds of the present invention in which the $R_3$-bearing carbon atom is in the R configuration are generally preferred.

The following specific compounds of the present invention are particularly preferred in their end-use application:

(R)-N-(2-Aminoethyl)-2-[4-[2-(2,3,6,9-tetrahydro-1,3-dipropyl-2,6-dioxo-1H-purin-8-yl)propyl]phenoxy]-acetamide;

(R)-N-(2-Aminoethyl)-2-[4-[1-(2,3,6,9-tetrahydro-1,3-dipropyl-2,6-dioxo-1H-purin-8-yl)propyl]phenoxy]-acetamide.

In addition to being useful as pharmaceutical agents, the compounds of the present invention are also useful as biochemical tools for studying the structure, function and binding characteristics of $A_1$ and $A_2$ receptor sites in mammalian tissues.

The following example provides an illustration of the utility of the compounds of the present invention. This example is intended to be illustrative only and does not limit the scope of the invention in any way.

EXAMPLE 24

Selective $A_1$-Adenosine Receptor Affinity of Various Novel 8-Substituted Purines Selective $A_1$-adenosine receptor Activity for various compounds of the present invention is demonstrated in Table 1. IC$_{50}$ values for $A_1$-adenosine receptor binding is determined according to the method of Goodman et al. [*Mol. Pharmacol.* 21:329-35, 1982]. IC$_{50}$ values for $A_2$-adenosine receptor binding is determined according to the method of Bruns et al. [*Mol. Pharmacol.* 29:331-46, 1986].

TABLE 1

$A_1$-and $A_2$-Adenosine Receptor Affinity Activity of 8-Substituted Purines

| Compound | IC$_{50}$ Adenosine $A_1$ (nM) | IC$_{50}$ Adenosine $A_2$ (nM) |
|---|---|---|
| 101673 | 1183 | >10,000 |
| 101699 | 327 | 5700 |
| 101345 | 14 | 36 |
| 102130 | 4.4 | 60 |
| 101993 | 60 | 1800 |
| 100991 | 10 | 300 |

101673 = 2-[4-[1-(2,3,6,9-Tetrahydro-1,3-dipropyl-2,6-dioxo-1H-purin-8-yl)propyl]phenoxy]acetic acid
101699 = 2-[4-[2-(2,3,6,9-Tetrahydro-1,3-dipropyl-2,6-dioxo-1H-purin-8-yl)propyl]phenoxy]acetic acid
101345 = N-(2-Aminoethyl)-2-[4-[2-(2,3,6,9-tetrahydro-1,3-dipropyl-2,6-dioxo-1H-purin-8-yl)propyl]phenoxy]-acetamide
102130 = N-(2-Aminoethyl)-2-[4-[1-(2,3,6,9-tetrahydro-1,3-dipropyl-2,6-dioxo-1H-purin-8-yl)propyl]phenoxy]-acetamide
101993 = (+)-N-(2-Aminoethyl)-2-[4-[2-(2,3,6,9-tetrahydro-1,3-dipropyl-2,6-dioxo-1H-purin-8-yl)propyl]phenoxy]-acetamide
100991 = (−)-N-(2-Aminoethyl)-2-[4-[2-(2,3,6,9-tetrahydro-1,3-dipropyl-2,6-dioxo-1H-purin-8-yl)propyl]phenoxy]-acetamide

What is claimed is:

1. A compound of the formula

[Chemical structure]

wherein
$R_1$, $R_2$ and $R_3$ are each independently a $C_1$-$C_4$ alkyl,
m is an integer 0, 1 or 2,
A is O or S,
n is an integer 1, 2 or 3, and
$R_4$ is H or a $C_1$-$C_4$ alkyl.

2. A compound of the formula

[Chemical structure]

wherein
$R_1$, $R_2$ and $R_3$ are each independently a $C_1$-$C_4$ alkyl,
m is an integer 0, 1 or 2,
A is O or S,
n is an integer 1, 2 or 3,
Y is —NH(CH$_2$)$_p$NH—,
p is an integer 2, 3 or 4

Z is a radical of the formula $$-\overset{O}{\underset{|}{C}}-\underset{R_5}{\overset{|}{CH}}-NH-$$

q is an integer 0, 1, 2 or 3, and
$R_5$ is a radical selected each time taken from the group consisting of H, $CH_3$, $-CH(CH_3)_2$, $-CH(CH_3)CH_2CH_3$, $-CH_2CH(CH_3)_2$, $-CH_2CH_2CH_2NH_2$, $-CH_2CH_2CH_2CH_2NH_2$, $-CH_2CH_2CH_2N=C(NH_2)_2$, $-CH_2CH_2CH_2CH_2N=C(NH_2)_2$, $-CH_2-\phantom{x}\text{C}_6\text{H}_4\text{-}NH_2$, or $-CH_2-\phantom{x}\text{C}_6\text{H}_4\text{-}N=C(NH_2)_2.$

3. A compound of the formula $$R_2\text{-}N\text{-}\underset{\underset{R_1}{|}}{\overset{O}{\underset{\|}{C}}}\text{-}\underset{NH}{\overset{N}{\underset{|}{C}}}\text{-}\underset{R_3}{\overset{|}{CH}}\text{-}(CH_2)_m\text{-}\phantom{x}\text{C}_6\text{H}_4\text{-}A\text{-}(CH_2)_n\text{-}\overset{O}{\overset{\|}{C}}\text{-}(Z)_q\text{-}OH$$

wherein
$R_1$, $R_2$ and $R_3$ are each independently a $C_1$-$C_4$ alkyl,
m is an integer 0, 1 or 2,
A is O or S,
n is an integer 1, 2 or 3,
Z is a radical of the formula $$-NH-\underset{R_5}{\overset{|}{CH}}-\overset{O}{\overset{\|}{C}}-$$

q is an integer 1, 2 or 3, and
$R_5$ is a radical selected each time taken from the group consisting of H, $CH_3$, $-CH(CH_3)_2$, $-CH(CH_3)CH_2CH_3$, $-CH_2CH(CH_3)_2$, $-CH_2CH_2CH_2NH_2$, $-CH_2CH_2CH_2CH_2NH_2$, $-CH_2CH_2CH_2N=C(NH_2)_2$, $-CH_2CH_2CH_2CH_2N=C(NH_2)_2$, $-CH_2-\phantom{x}\text{C}_6\text{H}_4\text{-}NH_2$, or $-CH_2-\phantom{x}\text{C}_6\text{H}_4\text{-}N=C(NH_2)_2.$

4. A method of providing a selective $A_1$-adenosine receptor antagonist effect in a patient in need thereof comprising administering to said patient a therapeutically effective $A_1$-antagonistic amount of a compound of claim 1, 2 or 3.

5. A method according to claim 4 wherein the patient is in need of treatment for Alzheimer's Disease.

6. A method according to claim 4 wherein the patient is in need of treatment for congestive heart failure.

7. A method according to claim 4 wherein the patient is in need of treatment for pulmonary bronchoconstriction.

8. A composition comprising an assayable amount of a compound of claim 1, 2 or 3 in admixture or otherwise in association with an inert carrier.

9. A pharmaceutical composition comprising an effective immunosuppressive amount of a compound of claim 1, 2 or 3 in admixture or otherwise in association with one or more pharmaceutically acceptable carriers or excipients.

10. A compound according claim 2 wherein the compound is N-(2-Aminoethyl)-2-[4-[2-(2,3,6,9-tetrahydro-1,3-dipropyl-2,6-dioxo-1H-purin-8-yl)propyl]phenoxy]-acetamide.

11. A compound according claim 2 wherein the compound is N-(2-Aminoethyl)-2-[4-[1-(2,3,6,9-tetrahydro-1,3-dipropyl-2,6-dioxo-1H-purin-8-yl)propyl]phenoxy]-acetamide.

12. A compound according to claim 2 wherein the compound is (+)-N-(2-aminoethyl)-2-[4-[2-(2,3,6,9-tetrahydro-1,3-dipropyl-2,6-dioxo-1H-purin-8-yl)propyl]-phenoxy]-acetamide.

13. A compound according to claim 2 wherein the compound is (−)-N-(2-aminoethyl)-2-[4-[2-(2,3,6,9-tetrahydro-1,3-dipropyl-2,6-dioxo-1H-purin-8-yl)propyl]-phenoxy]-acetamide.

* * * * *

UNITED STATES PATENT AND TRADEMARK OFFICE
CERTIFICATE OF CORRECTION

PATENT NO. : 5,208,240
DATED : May 4, 1993
INVENTOR(S) : Norton P. Peet, Nelsen L. Lentz and Mark W. Dudley It is certified that error appears in the above-identified patent and that said Letters Patent is hereby corrected as shown below:

At Column 8, line 8, the patent reads "an molar" and should read --a molar--.

At Column 8, line 10, the patent reads "a organic" and should read --an organic--.

At Column 16, line 35, the patent reads "hexamethylphos-phoramide" and should read --hexamethylphosphoramide--.

At Column 17, line 44, the patent reads "acid," and should read --acid---.

At Column 26, line 66 the patent reads "(85.49," and should read --(85.4g,--.

At Column 32, line 40, the patent reads "a additive" and should read --an additive--.

At Column 46, line 41, the patent reads "according claim" and should read --according to claim--.

At Column 46, line 45, the patent reads "according claim" and should read --according to claim--.

Signed and Sealed this

Sixteenth Day of August, 1994

Attest:

BRUCE LEHMAN

*Attesting Officer*   *Commissioner of Patents and Trademarks*